US006288027B1

(12) United States Patent
Gawryl et al.

(10) Patent No.: US 6,288,027 B1
(45) Date of Patent: *Sep. 11, 2001

(54) PRESERVING A HEMOGLOBIN BLOOD SUBSTITUTE WITH A TRANSPARENT OVERWRAP

(75) Inventors: Maria S. Gawryl, Charlestown; Robert A. Houtchens, Milford; William R. Light, Natick, all of MA (US)

(73) Assignee: Biopure Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/348,881

(22) Filed: Jul. 7, 1999

Related U.S. Application Data

(63) Continuation-in-part of application No. 09/173,189, filed on Oct. 14, 1998, which is a continuation-in-part of application No. 08/974,658, filed on Nov. 19, 1997, now abandoned, which is a continuation of application No. 08/471,583, filed on Jun. 7, 1995, now Pat. No. 5,691,452, which is a continuation-in-part of application No. 08/458,916, filed on Jun. 2, 1995, now Pat. No. 5,840,582, which is a continuation of application No. 08/409,337, filed on Mar. 23, 1995, now Pat. No. 5,854,209.

(51) Int. Cl.[7] .......................... C07K 14/805; A61K 19/02

(52) U.S. Cl. .............................. 514/6; 530/385; 604/403; 604/408

(58) Field of Search ........................... 530/385; 604/403, 604/408; 514/6

(56) References Cited

U.S. PATENT DOCUMENTS

| | | | |
|---|---|---|---|
| 4,001,200 | 1/1977 | Bonsen et al. ................ 260/112.5 R |
| 4,001,401 | 1/1977 | Bonsen et al. ........................ 424/177 |
| 4,053,590 | 10/1977 | Bonsen et al. ........................ 424/177 |
| 4,061,736 | 12/1977 | Morris et al. ........................ 424/177 |
| 4,140,162 | 2/1979 | Gajewski et al. ....................... 150/1 |
| 4,460,365 | 7/1984 | Gánshirt et al. ..................... 604/408 |
| 4,538,981 | 9/1985 | Venturini ............................... 431/190 |
| 4,561,110 | * 12/1985 | Herbert ................................ 604/403 |
| 4,670,417 | 6/1987 | Iwasaki et al. ........................ 514/6 |
| 4,699,816 | * 10/1987 | Galli et al. ............................. 428/40 |
| 4,704,402 | 11/1987 | Abraham et al. ................... 514/543 |
| 4,826,811 | 5/1989 | Sehgal et al. ............................ 514/6 |
| 4,826,955 | * 5/1989 | Akkapeddi et al. ................. 528/324 |
| 4,857,636 | 8/1989 | Hsia ..................................... 530/385 |
| 4,861,867 | 8/1989 | Estep ................................... 530/385 |
| 4,988,515 | 1/1991 | Buckberg ............................. 424/529 |
| 5,045,529 | 9/1991 | Chiang .................................... 514/6 |
| 5,051,353 | 9/1991 | Stratton et al. ........................ 435/2 |
| 5,084,558 | 1/1992 | Rausch et al. ....................... 530/385 |
| 5,100,401 | 3/1992 | Patel .................................... 604/410 |
| 5,167,657 | 12/1992 | Patel .................................... 604/410 |
| 5,178,884 | 1/1993 | Goodrich et al. ................... 424/533 |
| 5,189,146 | 2/1993 | Hsia ..................................... 530/385 |
| 5,194,590 | 3/1993 | Sehgal et al. ........................ 530/385 |
| 5,234,903 | * 8/1993 | Nho et al. ............................... 514/6 |
| 5,264,555 | 11/1993 | Shorr et al. .......................... 530/385 |
| 5,281,360 | * 1/1994 | Hong et al. ...................... 252/188.28 |
| 5,296,465 | 3/1994 | Rausch et al. ........................... 514/6 |
| 5,296,466 | 3/1994 | Kilbourn et al. ........................ 514/6 |
| 5,334,706 | 8/1994 | Przybelski ........................... 530/385 |
| 5,352,773 | 10/1994 | Kandler et al. ..................... 530/385 |
| 5,356,709 | 10/1994 | Woo et al. ........................... 428/376 |
| 5,439,882 | 8/1995 | Feola et al. ............................. 514/6 |
| 5,683,768 | 11/1997 | Shang et al. .......................... 428/35 |
| 5,929,031 | 7/1999 | Kerwin et al. ........................ 514/12 |
| 6,127,043 | 10/2000 | Lange .................................. 428/515 |

FOREIGN PATENT DOCUMENTS

| | | |
|---|---|---|
| 3915252A | 11/1990 | (DE) . |
| 2107191A | 4/1983 | (GB) . |
| WO89/12456 | 12/1989 | (WO) . |

OTHER PUBLICATIONS

Dodrill et al. 'Barrier Coated Polyester Film for Healthcare Packaging', Confrence Paper presented at the "Polyester in Healthcare Packaging", pp. 1–17, Oct. 1996.*

Biro, G. P., et al., "Early Deleterious Hemorheologic Changes Following Acute Experimental Coronary Occlusion and Salutary Antihyperviscosity Effect of Hemodilution with Stroma–Free Hemoglobin," *American Heart Journal*, 103(5): 870–878 (1982).

Biro, G. P., and Beresford–Kroeger, D., "The Effect of Hemodilution with Stroma–Free Hemoglobin and Dextran on Collateral Perfusion of Ischemic Myocardium in the Dog," *American Heart Journal*, 99(1): 64–75 (1980).

(List continued on next page.)

*Primary Examiner*—Christopher S. F. Low
*Assistant Examiner*—Anish Gupta
(74) *Attorney, Agent, or Firm*—Hamilton, Brook, Smith & Reynolds, P.C.

(57) ABSTRACT

The invention relates to a method for preserving the stability of a hemoglobin blood substitute comprising maintaining the hemoglobin blood substitute in an atmosphere substantially free of oxygen. The invention also involves a method for producing a stable polymerized hemoglobin blood-substitute from blood. The method of this invention includes mixing blood with an anticoagulent to form a blood solution, washing the red blood cells in the blood solution and then separating the washed red blood cells from the white blood cells. This method also includes disrupting the red blood cells to release hemoglobin and form a hemoglobin solution, which is then treated by high performance liquid chromatography to form a hemoglobin eluate. The hemoglobin eluate is then deoxygenated, contacted with a first sulfhydryl compound to form an oxidation-stabilized deoxygenated hemoglobin solution, and mixed with a cross-linking agent to form a polymerization reaction mixture, which is then polymerized. The polymerized hemoglobin solution is then diafiltered with a physiologic solution and with a sulfhydryl compound, whereby the polymerized hemoglobin solution is made physiologically acceptable, and whereby the sulfhydryl compound scavenges oxygen, to form a stable polymerized hemoglobin blood-substitute, which is then packaged and stored in an atmosphere substantially free of oxygen.

9 Claims, No Drawings

OTHER PUBLICATIONS

Cole, D. J., et al., "Focal Cerebral Ischemia in Rats: Effect of Hypervolemic Hemodilution with Diaspirin Cross–Linked Hemoglobin versus Albumin on Brain Injury and Edema," *Anesthesiology*, 78(2): 335–342 (1993).

Cole, D. J., et al., "Focal Cerebral Ischemia in Rats: Effect of Hemodilution with α–α Cross–Linked Hemoglobin on CBF," *J. Cereb. Blood Flow Metab.*, 12(6): 971–976 (1992).

Cole, D. J., et al., "Effect of Viscosity and Oxygen Content on Cerebral Blood Flow in Ischemic and Normal Rat Brain," *Journal of Neurological Science*, 124: 15–20 (1994).

Feola, M., et al., "Clinical Trial of a Hemoglobin Based Blood Substitute in Patients with Sickle Cell Anemia," *Surgery, Gynecology & Obstetrics*, 174: 379–386 (1992).

Feola, M., et al., "Improved Oxygenation of Ischemic Myocardium by Hemodilution with Stroma–Free Hemoglobin Solution," *Chest*, 75(3): 369–375 (1979).

Hauser, C. J., and Shoemaker, W. C., "Hemoglobin solution in the Treatment of Hemorrhagic Shock," *Critical Care Medicine*, 10(4): 283–287 (1982).

Homer, L. D., et al., "Oxygen Gradients Between Red Blood Cells in the Microcirculation," *Hypoxia Between Red Cells*, Academic Press, Inc. 308–323 (1981).

Leone, B. J., and Spahn, D. R., "Anemia, Hemodilution, and Oxygen Delivery," *Anesth. Analg.* 75: 651–653 (1992).

Sarelius, I. H., "Cell and Oxygen Flow in Arterioles Controlling Capillary Perfusion," *Am. J. Physiol.* 265 (*Heart Circ. Physiol. 34*): H1682–H1687 (1993).

Standl, T., et al., "Hemodynamics and Oxygen Transport During Complete Isovolemic Hemodilution With a New Ultrapurified Polymerized Bovine Hemoglobin Solution in a Dog Model." Paper presented at the Annual Meeting of the American Society of Anesthesiologists, Washington (1993) and at the Central European Congress of Anaesthesiology, Dresden (1993).

Tsai, A. G., and Intaglietta, M., "Local Tissue Oxygenation During Constant Red Blood Cell Flux: A Discrete Source Analysis of Velocity and Hematocrit Changes," *Microvascular Research 37*: 308–322 (1989).

Wei, E. P., et al., "Effect of Local Change in $O_2$ Saturation of Hemoglobin on Cerebral Vasodilation from Hypoxia and Hypotension," *Am. J. Physiol., 265* (*Heart Circ. Physiol. 34*): H1439–H1443 (1993).

Chu, D., et al., Abstract 80.13, "The Effect of Hemodilution with a Purified Monomer or Purified Bovine Hemoglobin on Infarct Size in Focal Ischemia in Rabbits," *Society for Neuroscience Abstracts*, 20:180 (1994), presented at the 24th Annual Meeting Society of Neuroscience, Miami Beach, FL (Nov. 13–18, 1994).

Teicher, et al., "J. Oxygenation of tumors by a hemoglobin solution," *J. Cancer Research and Clinical Onco 120*:85–90 (1993).

Paradis, et al., "Selective aortic perfusion and oxygenation: An effective adjunct to external chest compression–based cardiopulmonary resuscitation," *J. American College of Cardiology*, 23(2), 497–504 (1994).

Krieter, et al., "Effects of stroma–free polymerized bovine hemoglobin solution on oxygen transport, Global and regional blood flow in a canine model of stepwise hemodilution," *Anesth. Analg.*, 78(2) S226 (1994).

Waschke, et al., "Local Cerebral Blood Flow and Glucose Utilization After Blood Exchange with A Hemoglobin–Based $O_2$ Carrier in Conscious Rates," *Amer. J. Physiol.*, 265, H1243–H1248 (Jun. 1993).

E. Antonini, et al., "Sickling and Hemoglobin S Gelation." In *Methods in Enzymology Volume 76 Hemoglobins*, eds. (NY: Academic Press), pp. 765, 769–770 (1981).

"Film Preserves Blood Substitute," *Pharmaceutical & Medical Packaging News*, (Jul. 1998).

F. DeVenuto, "Stability of Hemoglobin Solution During Extended Storage," *J. Lab. Clin. Med.*, 92(6):946–952 (Dec. 1975).

P. Hamilton et al., "Preparation of Hemoglobin Solutions for Intravenous Infusion," *Hemoglobin Solution*, pp. 455–463.

Dodrill et al., "Barrier Coated Polyester Films for Healthcare Packaging," Conference Paper Presented at the Polester in Healthcare Packaging, pp. 1–17 (1996).

* cited by examiner

PRESERVING A HEMOGLOBIN BLOOD SUBSTITUTE WITH A TRANSPARENT OVERWRAP

RELATED APPLICATIONS

This Application is a Continuation-in-Part of copending U.S. patent application Ser. No. 09/173,189, filed on Oct. 14, 1998, which is a Continuation-in-Part of U.S. patent application Ser. No. 08/974,658, filed on Nov. 19, 1997 now abandoned, which is a Continuation of U.S. patent application Ser. No. 08/471,583, filed Jun. 7, 1995 now issued U.S. Pat. No. 5,691,452, which is a Continuation-in-Part of U.S. patent application Ser. No. 08/458,916, filed Jun. 2, 1995 now issued U.S. Pat. No. 5,840,582, which is a Continuation of U.S. patent application Ser. No. 08/409,337, filed Mar. 23, 1995 now issued U.S. Pat. No. 5,854,209.

BACKGROUND OF THE INVENTION

There exists a need for a blood-substitute to treat or prevent hypoxia resulting from blood loss (e.g, from acute hemorrhage or during surgical operations), resulting from anemia (e.g., pernicious anemia or sickle cell anemia), or resulting from shock (e.g, volume deficiency shock, anaphylactic shock, septic shock or allergic shock). The use of blood and blood fractions as in these capacities as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and interdonor incompatibility.

Human hemoglobin, as a blood-substitute, possesses osmotic activity and the ability to transport and transfer oxygen, but it has the disadvantage of rapid elimination from circulation by the renal route and through vascular walls, resulting in a very short, and therefore, a typically unsatisfactory half-life. Further, human hemoglobin is also frequently contaminated with toxic levels of endotoxins, bacteria and/or viruses.

Non-human hemoglobin suffers from the same deficiencies as human hemoglobin. In addition, hemoglobin from non-human sources is also typically contaminated with proteins, such as antibodies, which could cause an immune system response in the recipient.

Previously, at least four other types of blood-substitutes have been utilized, including perfluorochemicals, synthesized hemoglobin analogues, liposome-necapsulated hemoglobin, and chemically-modified hemoglobin. However, many of these blood-substitutes have typically had short intravascular retention times, being removed by the circulatory system as foreign substances or lodging in the liver, spleen, and other tissues. Also, many of these blood-substitutes have been biologically incompatible with living systems.

Thus, in spite of the recent advances in the preparation of hemoglobin-based blood-substitutes, the need has continued to exist for a blood-substitute which has levels of contaminants, such as endotoxins, bacteria, viruses, phospholipids and non-hemoglobin proteins, which are sufficiently low to generally prevent an immune system response and any toxicological effects resulting from an infusion of the blood-substitute. In addition, the blood-substitute must also be capable of transporting and transferring adequate amounts of oxygen to tissues under ambient conditions and must have a good intravascular retention time.

Further, it is preferred that the blood-substitute 1) has an oncotic activity generally equivalent to that of whole blood, 2) can be transfused to most recipients without cross-matching or sensitivity testing, and 3) can be stored with minimum amounts of refrigeration for long periods.

The blood-substitute is typically packaged in a metal foil laminate overwrap having high $O_2$ and moisture barrier properties. The metal foil laminates are typically opaque, thus not allowing visual inspection of the product nor inspection of the integrity of the primary package. Furthermore, an opaque overwrap requires the use of a second label on the outside of the overwrap.

In the past, clear silicon containing laminates with high oxygen and moisture barrier properties have not been useful in automated packaging equipment because the stress on the material caused it to crack or otherwise lose barrier properties.

SUMMARY OF THE INVENTION

The present invention is drawn to a method for preserving a deoxygenated hemoglobin blood substitute. The method comprises maintaining the deoxygenated hemoglobin blood substitute in an oxygen barrier film overwrap comprising a transparent laminate material having a thickness of between about 0.01 and about 0.005 inches. The oxygen barrier film overwrap of the present invention has an oxygen permeability of less than about 0.01 cubic centimeters per 100 square inches over 24 hours at one atmosphere and at room temperature. Room temperature is defined herein as 23° C.

The present invention also is drawn generally to a preserved, deoxygenated hemoglobin blood substitute comprising a deoxygenated hemoglobin blood substitute and a transparent oxygen barrier film overwrap package. The transparent oxygen barrier film overwrap package of the present invention comprises a first polymer layer, an oxygen barrier film and a second polymer layer. Said oxygen barrier film has an oxygen permeability of less than about 0.01 cubic centimeter per 100 square inches over 24 hours at one atmosphere and at room temperature, within which the deoxygenated hemoglobin blood substitute is sealed, thereby preserving the deoxygenated hemoglobin blood substitute in an environment that is substantially free of oxygen.

In one embodiment of the present invention, the clear overwrap film is used in combination with foil films in automated packaging. In one embodiment, a automated packaging machine manufactured by Tiromat (Avon, Mass.) has been used.

The advantages of this invention are numerous. One advantage is that the hemoglobin stored according to the methods of this invention has a greater degree of purity and longer shelf-life. High barrier overwraps provide an addition level of product quality even when high barrier primary packaging is employed. In addition, the transparent high barrier overwraps of the present invention provide extremely high oxygen and water vapor barrier properties but have no saran (polyvinylidene chloride, PVDC) layer. PVDC poses a medical waste problem because chlorinated products such as polycyclic aromatic hydrocarbons and hydrochloric acid are generated during incineration. Clear overwraps allow the label of the primary package to be seen. Therefore, a second label typically is not required on the overwrap. In addition, product quality inspection and primary package integrity can also be evaluated. Furthermore, as demonstrated for the first time herein, automation equipment can be used with the clear oxygen barrier laminates, allowing production of very large numbers of packages in a short period of time with very little human labor and without the loss of barrier properties. The blood-substitute remains stable at room temperature for periods of two years or more, a significant improvement over previous methods.

DETAILED DESCRIPTION OF THE INVENTION

The features and other details of the process of the invention will now be more particularly described and pointed out in the claims. It will be understood that the particular embodiments of the invention are shown by way of illustration and not as limitations of the invention. The principle features of this invention can be employed in various embodiments without departing from the scope of the present invention.

The invention relates to a method for preserving the stability of a hemoglobin blood substitute comprising maintaining the hemoglobin blood substitute in an atmosphere substantially free of oxygen. This method can be accomplished by maintaining the blood substitute in an oxygen-impermeable container, such as an polymer films, (e.g., an essentially oxygen-impermeable polyester, ethylene vinyl alcohol (EVOH), or nylon), and laminates thereof. Where the container is an oxygen barrier overwrap, the container can be manufactured from a variety of materials, including polymer films, (e.g., an essentially oxygen-impermeable polyester, ethylene vinyl alcohol (EVOH), or nylon) and laminates, such as a transparent laminate (e.g. a silicon oxide or EVOH containing laminate) or a metal foil laminate (e.g., a silver or aluminum foil laminate).

Where the overwrap is a film, such as a polyester film, the film can be rendered essentially oxygen-impermeable by a variety of suitable methods. In one embodiment, the film as manufactured is essentially oxygen-impermeable. Alternatively, where the polymeric material is not sufficiently oxygen-impermeable to meet the desired specifications, the film can be laminated or otherwise treated to reduce or eliminate the oxygen permeability.

In a preferred embodiment, a transparent laminate is employed for at least one face of the overwrap. In one embodiment, at least one layer of the transparent laminate is an oxygen barrier. The oxygen barrier layer preferably has a thickness between about 0.0001 and 0.001 inches. For both the primary package and the overwrap, the laminate typically contains one or more polymeric layers. The polymer can be a variety of polymeric materials including, for example, a polyester layer (e.g., a 48 gauge polyester), nylon or a polyolefin layer, such as polyethylene, ethylene vinyl acetate, or polypropylene or copolymers thereof.

The overwraps of the invention can be of a variety of constructions, including vials, cylinders, boxes, etc. In a preferred embodiment, the container is in the form of a bag. A suitable bag can be formed by continuously bonding one or more (e.g., two) sheets at the perimeter(s) thereof to form a tightly closed, oxygen impermeable, construction having a fillable center. The shape of the bag can be those routinely encountered in that art. In the case of laminates comprising polyolefins, such as linear low density, low density, medium or high density polyethylene or polypropylene and copolymers thereof, the perimeter of the bag is bonded or sealed using heat. It is well within the skill of the art to determine the appropriate temperature to generate a tightly closed, oxygen and/or moisture impermeable construction.

The containers preferably have an oxygen permeability of less than about 0.01 cc per 100 square inches per 24 hours per atmosphere at room temperature, preferably less than about 0.005 cc per square inch at these conditions. Containers that meet these criteria include for example plastic containers with an overwrap, such as high barrier laminate containers with an overwrap constructed, for example, from polyolefin, such as polypropylene, ethylene vinyl alcohol and another layer of polyolefin such as linear low density polyethylene laminate. In one embodiment the laminate comprises polypropylene, EVOH and polypropylene copolymer at thicknesses of 1.8 mil, 1.2 mil and 3.0 mil respectively. The oxygen permeability of the high barrier laminate is 0.00153 cc/100 in$^2$-atm-day (25° C., 100%/50% RH) and water vapor transmission is about 0.354 mg/100 in$^2$-atm-day (25° C., 100%/50% RH). These polymeric composite film overwrapped plastic bags are sealed using a Tiromat sealing apparatus (Avon, Mass.). In one embodiment, the bottom sheet of package is a foil and is formed into a dish shape. The product package is then placed onto the foil, with the label facing upward, the chamber holding the foil and package is then nitrogen purged and a vacuum pulled. The clear laminate is then heat sealed to the foil laminate bottom layer.

In a preferred embodiment, the blood substitute is packaged under an atmosphere which is substantially free of oxygen. Examples of suitable atmospheres include nitrogen, argon and helium.

As defined herein, a blood-substitute is a hemoglobin-based oxygen carrying composition for use in humans, mammals and other vertebrates, which is capable of transporting and transferring oxygen to vital organs and tissues, at least, and can maintain sufficient intravascular oncotic pressure. A vertebrate is as classically defined, including humans, or any other vertebrate animals which uses blood in a circulatory system to transfer oxygen to tissue. Additionally, the definition of circulatory system is as classically defined, consisting of the heart, arteries, veins and microcirculation including smaller vascular structures such as capillaries.

A blood-substitute of the invention preferably has levels of endotoxins, phospholipids, foreign proteins and other contaminants which will not result in a significant immune system response and which are non-toxic to the recipient. Preferably, a blood-substitute is ultrapure. Ultrapure as defined herein, means containing less than 0.5 EU/ml of endotoxin, less than 3.3 nmoles/ml phospholipids and little to no detectable levels of non-hemoglobin proteins, such as serum albumin or antibodies.

The term "endotoxin" refers to the cell-bound lipopolysaccharides, produced as a part of the outer layer of gram-negative bacterial cell walls, which under many conditions are toxic. When injected into animals, endotoxins can cause fever, diarrhea, hemorrhagic shock, and other tissue damage. Endotoxin unit (EU) has been defined by the United States Pharmacopeial Convention of 1983, page 3014, as the activity contained in 0.1 nanograms of U.S. reference standard lot EC-5. One vial of EC-5 contains 10,000 EU. Examples of suitable means for determining endotoxin concentrations in a blood-substitute include the method "Kinetic/Turbidimetric Limuus Amebocytic Lysate (LAL) 5000 Methodology" developed by Associates of Cape Cod, Woods Hole, Mass.

Stable polymerized hemoglobin, as defined herein, is a hemoglobin-based oxygen carrying composition which does not substantially increase or decrease in molecular weight distribution and/or in methemoglobin content during storage periods at suitable storage temperatures for periods of two years or more, and preferably for periods of two years or more, when stored in a low oxygen environment. Suitable storage temperatures for storage of one year or more are between about 0° C. and about 40° C. The preferred storage temperature range is between about 0° C. and about 25° C.

A suitable low oxygen environment, or an environment that is substantially oxygen-free, is defined as the cumulative amount of oxygen in contact with the bloodsubstitute, over a storage period of at least about two months, preferably at least about one year, or more preferably at least about two years which will result in a methemoglobin concentration of less than about 15% by weight in the blood-substitute. The cumulative amount of oxygen includes oxygen in leakage into the blood-substitute packaging and the original oxygen content of the blood-substitute and packaging.

Throughout this method, from red blood cell (RBC) collection until hemoglobin polymerization, blood solution, RBCs and hemoglobin are maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at 10±2° C.

In this method, portions of the components for the process for preparing a stable polymerized hemoglobin blood-substitute are sufficiently sanitized to produce a sterile product. Sterile is as defined in the art, specifically, that the solution meets United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Inconel.

Suitable RBC sources include human blood, bovine blood, ovine blood, porcine blood, blood from other vertebrates and transgenically-produced hemoglobin, such as the transgenic Hb described in *BIO/TECHNOLOGY*, 12: 55–59 (1994).

The blood can be collected from live or freshly slaughtered donors. One method for collecting bovine whole blood is described in U.S. Pat. Nos. 5,084,558 and 5,296,465, issued to Rausch et al. It is preferred that the blood be collected in a sanitary manner.

At or soon after collection, the blood is mixed with at least one anticoagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution.

It is understood that the blood solution source can be from a freshly collected sample or from an old sample, such as expired human blood from a blood bank. Further, the blood solution could previously have been maintained in frozen and/or liquid state. It is preferred that the blood solution is not frozen prior to use in this method.

In another embodiment, prior to introducing the blood solution to anticoagulants, antibiotic levels in the blood solution, such as penicillin, are assayed. Antibiotic levels are determined to provide a degree of assurance that the blood sample is not burdened with an infecting organism by verifying that the donor of the blood sample was not being treated with an antibiotic. Examples of suitable assays for antibiotics include a penicillin assay kit (Difco, Detroit, Mich.) employing a method entitled "Rapid Detection of Penicillin in Milk". It is preferred that blood solutions contain a penicillin level of less than or equal to about 0.008 units/ml. Alternatively, a herd management program to monitor the lack of disease in or antibiotic treatment of the cattle may be used.

Preferably, the blood solution is strained prior to or during the anticoagulation step, for example by straining, to remove large aggregates and particles. A 600 mesh screen is an example of a suitable strainer.

The RBCs in the blood solution are then washed by suitable means, such as by diafiltration or by a combination of discrete dilution and concentration steps with at least one solution, such as an isotonic solution, to separate RBCs from extracellular plasma proteins, such as serum albumins or antibodies (e.g., immunoglobulins (IgG)). It is understood that the RBCs can be washed in a batch or continuous feed mode.

Acceptable isotonic solutions are as known in the art and include solutions, such as a citrate/saline solution, having a pH and osmolarity which does not rupture the cell membranes of RBCs and which displaces the plasma portion of the whole blood. A preferred isotonic solution has a neutral pH and an osmolarity between about 285–315 mOsm. In a preferred embodiment, the isotonic solution is composed of an aqueous solution of sodium citrate dihydrate (6.0 g/l) and of sodium chloride (8.0 g/l).

Water which can be used in the method of invention includes distilled water, deionized water, water-for-injection (WFI) and/or low pyrogen water (LPW). WFI, which is preferred, is deionized, distilled water that meets U.S. Pharmacological Specifications for water-for-injection. WFI is further described in *Pharmaceutical Engineering*, 11, 15–23 (1991). LPW, which is preferred, is deionized water containing less than 0.002 EU/ml.

It is preferred that the isotonic solution be filtered prior to being added to the blood solution. Examples of suitable filters include a Millipore 10,000 Dalton ultrafiltration membrane, such as a Millipore Cat # CDUF 050 G1 filter or A/G Technology hollow fiber, 10,000 Dalton (Cat # UFP-10-C-85).

In a preferred embodiment, RBCs in the blood solution are washed by diafiltration. Suitable diafilters include microporous membranes with pore sizes which will separate RBCs from substantially smaller blood solution components, such as a 0.1 µm to 0.5 µm filter (e.g., a 0.2 µm hollow fiber filter, Microgon Krosflo II microfiltration cartridge). Concurrently, a filtered isotonic solution is added continuously (or in batches) as makeup at a rate equal to the rate (or volume) of filtrate lost across the diafilter. During RBC washing, components of the blood solution which are significantly smaller in diameter than RBCs, or are fluids such as plasma, pass through the walls of the diafilter in the filtrate. RBCs, platelets and larger bodies of the diluted blood solution, such as white blood cells, are retained and mixed with isotonic solution, which is added continuously or batchwise to form a dialyzed blood solution.

In a more preferred embodiment, the volume of blood solution in the diafiltration tank is initially diluted by the addition of a volume of a filtered isotonic solution to the diafiltration tank. Preferably, the volume of isotonic solution added is about equal to the initial volume of the blood solution.

In an alternate embodiment, the RBCs are washed through a series of sequential (or reverse sequential) dilution and concentration steps, wherein the blood solution is diluted by adding at least one isotonic solution, and is concentrated by flowing across a filter, thereby forming a dialyzed blood solution.

RBC washing is complete when the level of plasma proteins contaminating the RBCs has been substantially reduced (typically at least about 90%). Typically, RBC washing is complete when the volume of filtrate drained from diafilter 34 equals about 300%, or more, of the volume of blood solution contained in the diafiltration tank prior to diluting the blood solution with filtered isotonic solution. Additional RBC washing may further separate extracellular plasma proteins from the RBCs. For instance, diafiltration with 6 volumes of isotonic solution may remove at least about 99% of IgG from the blood solution.

The dialyzed blood solution is then exposed to means for separating the RBCs in the dialyzed blood solution from the white blood cells and platelets, such as by centrifugation.

It is understood that other methods generally known in the art for separating RBCs from other blood components can be employed. For example, sedimentation, wherein the separation method does not rupture the cell membranes of a significant amount of the RBCs, such as less than about 30% of the RBCs, prior to RBC separation from the other blood components.

Following separation of the RBCs, the RBCs are lysed by a means for lysing RBCs to release hemoglobin from the RBCs to form a hemoglobin-containing solution.

Lysis means can use various lysis methods, such as mechanical lysis, chemical lysis, hypotonic lysis or other known lysis methods which release hemoglobin without significantly damaging the ability of the Hb to transport and release oxygen.

In yet another embodiment, recombinantly produced hemoglobin, such as the recombinantly produced hemoglobin described in *Nature*, 356: 258–260 (1992), can be processed in the method of invention in place of RBCs. The bacteria cells containing the hemoglobin are washed and separated from contaminants as described above. These bacteria cells are then mechanically ruptured by means known in the art, such as a ball mill, to release hemoglobin from the cells and to form a lysed cell phase. This lysed cell phase is then processed as is the lysed RBC phase.

Following lysis, the lysed RBC phase is then ultrafiltered to remove larger cell debris, such as proteins with a molecular weight above about 100,000 Daltons. Generally, cell debris include all whole and fragmented cellular components with the exception of Hb, smaller cell proteins, electrolytes, coenzymes and organic metabolic intermediates. Acceptable ultrafilters include, for example, 100,000 Dalton filters made by Millipore (Cat # CDUF 050 H1) and made by A/G Technology (Needham, Mass.; Model No. UFP100E55).

It is preferred that ultrafiltration continues until the concentration of Hb in the lysed RBC phase is less than 8 grams/liter (g/l) to maximize the yield of hemoglobin available for polymerization. Other methods for separating Hb from the lysed RBC phase can be employed, including sedimentation, centrifugation or microfiltration.

The Hb ultrafiltrate can then be ultrafiltered to remove smaller cell debris, such as electrolytes, coenzymes, metabolic intermediates and proteins less than about 30,000 Daltons in molecular weight, and water from the Hb ultrafiltrate. Suitable ultrafilters include a 30,000 Dalton ultrafilter (Millipore Cat # CDUF 050 T1 and/or Armicon, # 540 430).

The concentrated Hb solution can then be directed into one or more parallel chromatographic columns to further separate the hemoglobin by high performance liquid chromatography from other contaminants such as antibodies, endotoxins, phospholipids and enzymes and viruses. Examples of suitable media include anion exchange media, cation exchange media, hydrophobic interaction media and affinity media. In a preferred embodiment, chromatographic columns contain an anion exchange medium suitable to separate Hb from non-hemoglobin proteins. Suitable anion exchange mediums include, for example, silica, alumina, titania gel, cross-linked dextran, agarose or a derivatized moiety, such as a polyacrylamide, a polyhydroxyethyl-methacrylate or a styrene divinylbenzene, that has been derivatized with a cationic chemical functionality, such as a diethylaminoethyl or quaternary aminoethyl group. A suitable anion exchange medium and corresponding eluants for the selective absorption and desorption of Hb as compared to other proteins and contaminants, which are likely to be in a lysed RBC phase, are readily determinable by one of reasonable skill in the art.

In a more preferred embodiment, a method is used to form an anion exchange media from silica gel, which is hydrothermally treated to increase the pore size, exposed to γ-glycidoxy propylsilane to form active epoxide groups and then exposed to $C_3H_7(CH_3)NCl$ to form a quaternary ammonium anion exchange medium. This method is described in the *Journal of Chromatography*, 120:321–333 (1976), which is incorporated herein by reference in its entirety.

Chromatographic columns are first pre-treated by flushing with a first eluant which facilitates Hb binding. Concentrated Hb solution is then injected onto the medium in the columns. After injecting the concentrated Hb solution, the chromatographic columns are then successively washed with different eluants to produce a separate, purified Hb eluate.

In a preferred embodiment, a pH gradient is used in chromatographic columns to separate protein contaminants, such as the enzyme carbonic anhydrase, phospholipids, antibodies and endotoxins from the Hb. Each of a series of buffers having different pH values, are sequentially directed to create a pH gradient within the medium in the chromatographic column. It is preferred that the buffers be filtered, such as with a 10,000 Dalton depyrogenation membrane. The buffers used to separate Hb should have a low ionic strength such that elution of Hb and non-hemoglobin contaminants is generally dependent upon pH and not significantly dependent upon ionic strength. Typically, buffers with an ionic concentration of about 50 mM, or less, have suitable low ionic strengths.

The first buffer transports the concentrated Hb solution into the medium in the chromatographic columns and facilitates binding of the Hb to the medium. The second buffer then adjusts the pH within the columns to elute contaminating non-hemoglobin components while maintaining the Hb bound to the medium. The third buffer then elutes the Hb. The Hb eluate is then collected. It is preferred that the Hb eluate be directed through a sterile filter. Suitable sterile filters include 0.22 µm filters, such as a Sartorius Sartobran Cat # 5232507 G1PH filter.

In a preferred embodiment, the first 3%-to-4% of the Hb eluate and the last 3%-to-4% of the Hb eluate are directed to waste to provide assurance of the purity of the Hb eluate.

Wherein the chromatographic columns are to be reused, contaminating non-hemoglobin proteins and endotoxin, remaining in the columns, are then eluted by a fourth buffer.

The use of pH gradients to separate Hb form non-hemoglobin contaminants is further described in U.S. Pat.

No. 5,691,452, filed Jun. 7, 1995, which are incorporated herein by reference.

In a preferred embodiment, the first buffer is a tris-hydroxymethyl aminomethane (Tris) solution (concentration about 2 mM; pH about 8.4 to about 9.4). The second buffer is a mixture of the first buffer and a third buffer, with the second buffer having a pH of about 8.2 to about 8.6. The third buffer is a Tris solution (concentration about 50 mM; pH about 6.5 to about 7.5). The fourth buffer is a NaCl/Tris solution (concentrations about 1.0 M NaCl and about 20 mM Tris; pH about 8.4 to about 9.4, preferably about 8.9–9.1). It is particularly preferred that the pH of the second buffer be between about 8.2 and about 8.4.

Typically, the buffers used are at a temperature between about 0° C. and about 50° C. Preferably, buffer temperature is about 12.4±1.0° C. during use. In addition, the buffers are typically stored at a temperature of about 9° C. to about 11° C.

The Hb eluate is then preferably deoxygenated prior to polymerization to form a deoxygenated Hb solution (hereinafter deoxy-Hb)by means that substantially deoxygenate the Hb without significantly reducing the ability of the Hb in the Hb eluate to transport and release oxygen, such as would occur from denaturation of formation of oxidized hemoglobin (metHb).

In one embodiment, the Hb eluate is deoxygenated by gas transfer of an inert gas across a phase membrane. Such inert gases include, for example, nitrogen, argon and helium. It is understood that other means for deoxygenating a solution of hemoglobin, which are known in the art, can be used to deoxygenate the Hb eluate. Such other means, can include, for example, nitrogen sparging of the Hb eluate, chemical scavenging with reducing agents such as N-acetyl-L-cysteine (NAC), cysteine, sodium dithionite or ascorbate, or photolysis by light.

Following elution from the chromatographic column, the Hb eluate is preferably concentrated to improve the efficiency of the process. The Hb eluate is recirculated through an ultrafilter to concentrate the Hb eluate to form a concentrated Hb solution. Suitable ultrafilters include, for example, 30,000 or less Dalton ultrafilters (e.g., Millipore Helicon, Cat # CDUF050G1 or Amicon Cat # 540430). Typically, concentration of the Hb eluate is complete when the concentration of Hb is between about 100 to about 120 g/l. While concentrating the Hb eluate, the Hb eluate temperature is preferably maintained at approximately 8–12° C.

Buffer is then directed into the Hb solution, which is preferably concentrated, to adjust the ionic strength of the Hb solution to enhance Hb deoxygenation. It is preferred that the ionic strength be adjusted to between about 150 meq/l and about 200 meq/l to reduce the oxygen affinity of the Hb in the Hb solution. Suitable buffers include buffers with a pH that will not result in significant denaturing of the Hb protein but will have an ionic strength sufficiently high to promote Hb deoxygenation. Examples of suitable buffers include saline solutions with a pH range of about 6.5 to about 8.9. A preferred buffer is an aqueous 1.0 M NaCl, 20 mM Tris solution with a pH of about 8.9.

Preferably, the resulting buffered Hb solution is then recirculated through the ultrafilter, to again concentrate the Hb solution to improve the efficiency of the process. In a preferred embodiment, concentration is complete when the concentration of Hb is about 100 g/l to about 120 g/l.

During deoxygenation the Hb solution is circulated through a suitable phase transfer membrane. Appropriate phase transfer membranes include, for example, a 0.05 μm polypropylene hollow fiber microfilter (e.g., Hoechst-Celanese Cat # 5PCM-107). Concurrently, a counterflow of an inert gas is passed across the phase transfer membrane. Suitable inert gases include, for example, nitrogen, argon and helium. Gas exchange across the phase transfer membrane thereby strips oxygen out of the Hb solution.

Deoxygenation continues until the $pO_2$ of the Hb solution is reduced to a level wherein the oxygenated Hb (oxyhemoglobin or $HbO_2$) content in the Hb solution is about 20% or less. In a preferred embodiment, the $HbO_2$ content in the Hb solution is about 10% or less.

During deoxygenation, the temperature of the Hb solution is typically maintained at a level that will balance the rate of deoxygenation against the rate of methemoglobin formation. Temperature is maintained to limit methemoglobin content to less than 20%. An optimum temperature will result in less than about 5% methemoglobin content, and preferably less than about 2.5% methemoglobin content, while still deoxygenating the Hb solution. Typically, during deoxygenation the temperature of the Hb solution is maintained between about 19° C. and about 31° C.

During deoxygenation, and subsequently throughout the remaining steps of the method of invention, the Hb is maintained in a low oxygen environment to minimize oxygen absorption by the Hb and to maintain an $HbO_2$ content of less than about 20%, preferably less than about 10%.

The deoxygenated-Hb is then preferably equilibrated with a low oxygen content storage buffer, containing a sulfhydryl compound, to form an oxidation-stabilized deoxy-Hb. Suitable sulfhydryl compounds include non-toxic reducing agents, such as N-acetyl-L-cysteine (NAC) D,L-cysteine, γ-glutamyl-cysteine, glutathione, 2,3-dimercapto-1-propanol, 1,4-butanedithiol, thioglycolate, and other biologically compatible sulfhydryl compounds. The oxygen content of a low oxygen content storage buffer must be low enough not to significantly reduce the concentration of sulfhydryl compound in the buffer and to limit oxyhemoglobin content in oxidation stabilized deoxy-Hb to about 20% or less, preferably less than about 10%. Typically, the storage buffer has a $pO_2$ of less than about 50 torr.

In a preferred embodiment, the storage buffer should have a pH suitable to balance Hb polymerization and methemoglobin formation, typically between about 7.6 and about 7.9.

The amount of a sulfhydryl compound mixed with the deoxy-Hb is an amount high enough to increase intramolecular cross-linking of Hb during polymerization and low enough not to significantly decrease intermolecular cross-linking of Hb molecules, due to a high ionic strength. Typically, about one mole of sulfhydryl functional groups (-SH) are needed to oxidation stabilize between about 0.25 moles to about 5 moles of deoxy-Hb.

In a preferred embodiment, the storage buffer contains approximately 25–35 mM sodium phosphate buffer (pH 7.7–7.8) and contains an amount of NAC such that the concentration of NAC in oxidation stabilized deoxy-Hb is between about 0.003% and about 0.3%, by weight. More preferably, the NAC concentration in the oxidation stabilized deoxy-Hb is between about 0.05% and about 0.2% by weight.

Preferably, the storage buffer is filtered prior to mixing with the deoxy-Hb, such as through a 10,000 Dalton ultrafiltration membrane (Millipore Helicon Cat # CDUF050G1 or A/G Technology Maxcell Cat # UFP-10-C-75).

In one embodiment, the oxidation-stabilized deoxy-Hb then flows through an optional filter. Suitable filters include a 0.2 μm polypropylene prefilter and a 0.5 μm sterile microfilter (Pall Profile II, Cat # ABIY005Z7 or Gelman Supor). The deoxy-Hb is maintained under a substantially oxygen-free atmosphere. This can be accomplished, for example, by purging and blanketing the process apparatus with an inert gas, such as nitrogen, prior to and after filling with oxidation-stabilized deoxy-Hb.

Optionally, prior to transferring the oxidation-stabilized deoxy-Hb to polymerization, an appropriate amount of water is added to the polymerization reactor. In one embodiment an appropriate amount of water is that amount which would result in a solution with a concentration of about 10 to about 100 g/l Hb when the oxidation stabilized deoxy-Hb is added to the polymerization reactor. Preferably, the water is oxygen-depleted.

After the $PO_2$ of the water in the polymerization step is reduced to a level sufficient to limit $HbO_2$ content to about 20%, typically less than about 50 torr, the polymerization reactor is blanketed with an inert gas, such as nitrogen. The oxidation-stabilized deoxy-Hb is then transferred into the polymerization reactor, which is concurrently blanketed with an appropriate flow of an inert gas.

The temperature of the oxidation-stabilized deoxy-Hb solution in polymerization reactor is raised to a temperature to optimize polymerization of the oxidation-stabilized deoxy-Hb when contacted with a cross-linking agent. Typically, the temperature of the oxidation-stabilized deoxy-Hb is about 25° C. to about 45° C., and preferably about 41° C. to about 43° C. throughout polymerization. An example of an acceptable heat transfer means for heating the polymerization reactor is a jacketed heating system which is heated by directing hot ethylene glycol through the jacket.

The oxidation-stabilized deoxy-Hb is then exposed to a suitable cross-linking agent at a temperature sufficient to polymerize the oxidation-stabilized deoxy-Hb to form a solution of polymerized hemoglobin (poly(Hb)) over a period of about 2 hours to about 6 hours.

Examples of suitable cross-linking agents include polyfunctional agents that will cross-link Hb proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bis-imidate class, the acyl diazide class or the aryl dihalide class, among others.

A suitable amount of a cross-linking agent is that amount which will permit intramolecular cross-linking to stabilize the Hb and also intermolecular cross-linking to form polymers of Hb, to thereby increase intravascular retention. Typically, a suitable amount of a cross-linking agent is that amount wherein the molar ratio of cross-linking agent to Hb is in excess of about 2:1. Preferably, the molar ratio of cross-linking agent to Hb is between about 20:1 to 40:1.

Preferably, the polymerization is performed in a buffer with a pH between about 7.6 to about 7.9, having a chloride concentration less than or equal to about 35 mmolar.

In a preferred embodiment, a suitable amount of the cross-linking agent is added to the oxidation-stabilized deoxy-Hb and then mixed by a means for mixing with low shear. A suitable low-shear mixing means includes a static mixer. A suitable static mixer is, for example, a "Kenics" static mixer obtained from Chemineer, Inc.

In one embodiment, recirculating the oxidation-stabilized deoxy-Hb and the cross-linking agent through the static mixer causes turbulent flow conditions with generally uniform mixing of the cross-linking agent with the oxidation-stabilized deoxy-Hb thereby reducing the potential for forming pockets of deoxy-Hb containing high concentrations of the cross-linking agent. Generally uniform mixing of the cross-linking agent and the deoxy-Hb reduces the formation of high molecular weight Hb polymers, i.e. polymers weighing more than 500,000 Daltons, and also permits faster mixing of the cross-linking agent and the deoxy-Hb during polymerization. Furthermore, significant Hb intramolecular cross-linking will result during Hb polymerization due to the presence of a sulfhydryl compound, preferably NAC. While the exact mechanism of the interaction of the sulfhydryl compound with glutaraldehyde and/or Hb is not known, it is presumed that the sulfhydryl compound affects Hb/cross-linking agent chemical bonding in a manner that at least partially inhibits the formation of high molecular weight Hb polymers and preferentially forms stabilized tetrameric Hb.

Poly(Hb) is defined as having significant intramolecular cross-linking if a substantial portion (e.g., at least about 50%) of the Hb molecules are chemically bound in the poly(Hb), and only a small amount, such as less than about 15% are contained within high molecular weight polymerized hemoglobin chains. High molecular weight poly(Hb) molecules are molecules, for example, with a molecular weight above about 500,000 Daltons.

In a preferred embodiment, glutaraldehyde is used as the cross-linking agent. Typically, about 10 to about 70 grams of glutaraldehyde are used per kilogram of oxidation-stabilized deoxy-Hb. More preferably, glutaraldehyde is added over a period of five hours until approximately 29–31 grams of glutaraldehyde are added for each kilogram of oxidation-stabilized deoxy-Hb.

After polymerization, the temperature of the poly(Hb) solution in polymerization reactor is typically reduced to about 15° C. to about 25° C.

Wherein the cross-linking agent used is not an aldehyde, the poly(Hb) formed is generally a stable poly(Hb). Wherein the cross-linking agent used is an aldehyde, the poly(Hb) formed is generally not stable until mixed with a suitable reducing agent to reduce less stable bonds in the poly(Hb) to form more stable bonds. Examples of suitable reducing agents include sodium borohydride, sodium cyanoborohydride, sodium dithionite, trimethylamine, t-butylamine, morpholine borane and pyridine borane. Prior to adding the reducing agent, the poly(Hb) solution is optionally concentrated by ultrafiltration until the concentration of the poly(Hb) solution is increased to between about 75 and about 85 g/l. An example of a suitable ultrafilter is a 30,000 Dalton filter (e.g., Millipore Helicon, Cat # CDUF050LT and Amicon, Cat # 540430).

The pH of the poly(Hb) solution is then adjusted to the alkaline pH range to preserve the reducing agent and to prevent hydrogen gas formation, which can denature Hb during the subsequent reduction. In one embodiment, the pH is adjusted to greater than 10. The pH can be adjusted by adding a buffer solution to the poly(Hb) solution during or after polymerization. The poly(Hb) is typically purified to remove nonpolymerized hemoglobin. This can be accomplished by dialfiltration or hydroxyapatite chromatography (see, e.g. U.S. Pat. No. 5,691,453, which is incorporated herein by reference).

Following pH adjustment, at least one reducing agent, preferably a sodium borohydride solution, is added to the polymerization step typically through the deoxygenation loop. Typically, about 5 to about 18 moles of reducing agent are added per mole of Hb tetramer (per 64,000 Daltons of Hb) within the poly(Hb). In a preferred embodiment, for every nine liters of poly(Hb) solution in polymerization subsystem 98, one liter of 0.25 M sodium borohydride solution is added at a rate of 0.1 to 0.12 lpm.

The pH and electrolytes of the stable poly(Hb) can then be restored to physiologic levels to form a stable polymerized hemoglobin blood-substitute, by diafiltering the stable poly(Hb) with a diafiltration solution having a suitable pH and physiologic electrolyte levels. Preferably, the diafiltration solution is a buffer solution.

Wherein the poly(Hb) was reduced by a reducing agent, the diafiltration solution has an acidic pH, preferably between about 4 to about 6.

A non-toxic sulfhydryl compound can also be added to the stable poly(Hb) solution as an oxygen scavenger to enhance the stability of the final polymerized hemoglobin blood-substitute. The sulfhydryl compound can be added as part of the diafiltration solution and/or can be added separately. An amount of sulfhydryl compound is added to establish a sulfhydryl concentration which will scavenge oxygen to maintain methemoglobin content less than about 15% over the storage period. Preferably, the sulfhydryl compound is NAC. Typically, the amount of sulfhydryl compound added is an amount sufficient to establish a sulfhydryl concentration between about 0.05% and about 0.2% by weight.

In a preferred embodiment, the blood-substitute is packaged under aseptic handling conditions while maintaining pressure with an inert, substantially oxygen-free atmosphere, in the polymerization reactor and remaining transport apparatus.

The specifications for a suitable stable polymerized hemoglobin blood-substitute formed by the method of invention are provided in Table I.

TABLE I

| PARAMETER | RESULTS |
| --- | --- |
| pH (18–22° C.) | Physiologically acceptable |
| Endotoxin | Physiologically acceptable |
| Sterility Test | Meets Test |
| Phospholipids[a] | Physiologically acceptable |
| Total Hemoglobin | 10–250 g/l |
| Methemoglobin | <15% |
| Oxyhemoglobin | <10% |
| Sodium, $Na^+$ | Physiologically acceptable |
| Potassium, $K^+$ | |
| Chloride, $Cl^-$ | |
| Calcium, $Ca^{++}$ | |
| Boron | |
| Glutaraldehyde | Physiologically acceptable |
| N-acetyl-L-cysteine | Physiologically Acceptable |
| M.W. > 500,000 | ≦15% |
| M.W. ≦ 65,000 | <10% |
| M.W. <32,000 | <5% |
| Particulate Content >10μ | <12/ml |
| Particulate Content >25μ | <2/ml |

[a]measured in Hb before polymerization

The stable blood-substitute is then stored in a short-term storage container or into sterile storage containers, each having a low oxygen environment as described in detail above. The storage container should also be sufficiently impermeable to water vapor passage to prevent significant concentration of the blood-substitute by evaporation over the storage period. Significant concentration of the blood-substitute is concentration resulting in one or more parameters of the blood-substitute being high out of specification.

The synthesis of a stable polymerized hemoglobin blood-substitute, formed according to the method of invention, is further described in U.S. Pat. No. 5,296,465.

Vertebrates which can receive the blood-substitute, formed by the methods of the invention include mammals, such as a human, non-human primate, a dog, a cat, a rat, a horse or a sheep. Further, vertebrates, which can receive said blood-substitute, includes fetuses (prenatal vertebrate), postnatal vertebrates, or vertebrates at time of birth.

A blood-substitute of the present invention can be administered into the circulatory system by injecting the blood-substitute directly and/or indirectly into the circulatory system of the vertebrate, by one or more injection methods. Examples of direct injection methods include intravascular injections, such as intravenous and intraarterial injections, and intracardiac injections. Examples of indirect injection methods include intraperitoneal injections, subcutaneous injections, such that the blood-substitute will be transported by the lymph system into the circulatory system or injections into the bone marrow by means of a trocar or catheter. Preferably, the blood-substitute is administered intravenously.

The vertebrate being treated can be normovolemic, hypervolemic or hypovolemic prior to, during, and/or after infusion of the blood-substitute. The blood-substitute can be directed into the circulatory system by methods such as top loading and by exchange methods.

A blood-substitute can be administered therapeutically, to treat hypoxic tissue within a vertebrate resulting from many different causes including reduced RBC flow in a portion of, or throughout, the circulatory system, anemia and shock. Further, the blood-substitute can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to therapeutically or prophylactically treat hypoxia, particularly from a partial arterial obstruction or from a partial blockage in microcirculation, and the dosages used therein, is provided in copending U.S. patent application Ser. No. 08/409,337, filed Mar. 23, 1995, which is incorporated herein by reference in its entirety.

Typically, a suitable dose, or combination of doses of blood-substitute, is an amount which when contained within the blood plasma will result in a total hemoglobin concentration in the vertebrate's blood between about 0.1 to about 10 grams Hb/dl, or more, if required to make up for large volume blood losses.

The invention will now be further and specifically described by the following examples.

EXAMPLE 1

Synthesis of Stable Polymerized Hb Blood-Substitute

As described in U.S. Pat. No. 5,296,465, samples of bovine whole blood were collected, mixed with a sodium citrate anticoagulant to form a blood solution.

Each blood solution sample was maintained after collection at a temperature of about 2° C. and then strained to remove large aggregates and particles with a 600 mesh screen.

Prior to pooling, the penicillin level in each blood solution sample was assayed with an assay kit purchased from Difco, Detroit, Mich. using the method entitled "Rapid Detection of Penicillin in Milk" to ensure that penicillin levels in the blood solutions were <0.008 units/ml.

The blood solution samples were then pooled and mixed with depyrogenated aqueous sodium citrate solution to form a 0.2% by weight solution of sodium citrate in bovine whole blood (hereafter "0.2% sodium citrate blood solution").

The 0.2% sodium citrate blood solution was then passed, in-series, through 800 µm and 50 µm polypropylene filters to remove large blood solution debris of a diameter approximately 50 µm or more.

The RBCs were then washed to separate extracellular plasma proteins, such as BSA or IgG, from the RBCs. To wash the RBCs contained in the blood solution, the volume of blood solution in the diafiltration tank was initially diluted by the addition of an equal volume of a filtered isotonic solution to diafiltration tank. The isotonic solution was filtered with a Millipore (Cat # CDUF 050 G1) 10,000 Dalton ultrafiltration membrane. The isotonic solution was composed of 6.0 g/l sodium citrate dihydrate and 8.0 g/l sodium chloride in water-for-injection (WFI).

The diluted blood solution was then concentrated back to its original volume by diafiltration through a 0.2 µm hollow fiber (Microgon Krosflo II microfiltration cartridge) diafilter. Concurrently, filtered isotonic solution was added continuously, as makeup, at a rate equal to the rate of filtrate loss through the 0.2 µm diafilter. During diafiltration, components of the diluted blood solution which were significantly smaller in diameter than RBCs, or are fluids such as plasma, passed through the walls of the 0.2 µm diafilter with the filtrate. RBCs, platelets and larger bodies of the diluted blood solution, such as white blood cells, were retained with continuously-added isotonic solution to form a dialyzed blood solution.

During RBC washing, the diluted blood solution was maintained at a temperature between approximately 10 to 25° C. with a fluid pressure at the inlet of the diafilter between about 25 psi and about 30 psi to improve process efficiency.

RBC washing was complete when the volume of filtrate drained from the diafilter equaled about 600% of the volume of blood solution prior to diluting with filtered isotonic solution.

The dialyzed blood solution was then continuously pumped at a rate of approximately 4 lpm to a Sharples Super Centrifuge, Model # AS-16, fitted with a #28 ringdam. The centrifuge was operating while concurrently being fed dialyzed blood solution, to separate the RBCs from the white blood cells and platelets. During operation, the centrifuge rotated at a rate sufficient to separate the RBCs into a heavy RBC phase, while also separating a substantial portion of the white blood cells (WBCs) and platelets into a light WBC phase, specifically about 15,000 rpm. A fraction of the RBC phase and of the WBC phase were separately and continuously discharged from the centrifuge during operation.

Following separation of the RBCs, the RBCs were lysed to form a hemoglobin-containing solution. A substantial portion of the RBCs were mechanically lysed while discharging the RBCs from the centrifuge. The cell membranes of the RBCs ruptured upon impacting the wall of RBC phase discharge line at an angle to the flow of RBC phase out of the centrifuge, thereby releasing hemoglobin (Hb) from the RBCs into the RBC phase.

The lysed RBC phase then flowed through the RBC phase discharge line into a static mixer (Kenics ½ inch with 6 elements, Chemineer, Inc.). Concurrent with the transfer of the RBC phase to the static mixer, an equal amount of WFI was also injected into the static mixer, wherein the WFI mixed with the RBC phase. The flow rates of the RBC phase and the WFI into the static mixer are each at about 0.25 lpm.

Mixing the RBC phase with WFI in the static mixer produced a lysed RBC colloid. The lysed RBC colloid was then transferred from the static mixer into a Sharples Super Centrifuge (Model # AS-16, Sharples Division of Alfa-Laval Separation, Inc.) which was suitable to separate the Hb from non-hemoglobin RBC components. The centrifuge was rotated at a rate sufficient to separate the lysed RBC colloid into a light Hb phase and a heavy phase. The light phase was composed of Hb and also contained non-hemoglobin components with a density approximately equal to or less than the density of Hb.

The Hb phase was continuously discharged from the centrifuge, through a 0.45 µm Millipore Pellicon Cassette, Cat # HVLP 000 C5 microfilter, and into a holding tank in preparation for Hb purification. Cell stroma were then returned with the retentate from the microfilter to the holding tank. During microfiltration, the temperature within the holding tank was maintained at 10° C. or less. To improve efficiency, when the fluid pressure at the microfilter inlet increased from an initial pressure of about 10 psi to about 25 psi, microfiltration was complete. The Hb microfiltrate was then transferred from the microfilter into the microfiltrate tank.

Subsequently, the Hb microfiltrate was pumped through a 100,000 Millipore Cat # CDUF 050 H1 ultrafilter. A substantial portion of the Hb and water, contained in the Hb microfiltrate, permeated the 100,000 Dalton ultrafilter to form a Hb ultrafiltrate, while larger cell debris, such as proteins with a molecular weight above about 100,000 Dalton, were retained and recirculated back into the microfiltrate tank. Concurrently, WFI was continuously added to the microfiltrate tank as makeup for water lost in the ultrafiltrate. Generally, cell debris include all whole and fragmented cellular components with the exception of Hb, smaller cell proteins, electrolytes, coenzymes and organic metabolic intermediates. Ultrafiltration continued until the concentration of Hb in the microfiltrate tank was less than 8 grams/liter (g/l). While ultrafiltering the Hb, the internal temperature of the microfiltrate tank was maintained at about 10° C.

The Hb ultrafiltrate was transferred into an ultrafiltrate tank, wherein the Hb ultrafiltrate was then recirculated through a 30,000 Dalton Millipore Cat # CDUF 050 T1 ultrafilter to remove smaller cell components, such as electrolytes, coenzymes, metabolic intermediates and proteins less than about 30,000 Daltons in molecular weight, and water from the Hb ultrafiltrate, thereby forming a concentrated Hb solution containing about 100 g Hb/l.

The concentrated Hb solution was then directed from the ultrafiltrate tank onto the media contained in parallel chromatographic columns (2 feet long with an 8 inch inner diameter) to separate the Hb by high performance liquid chromatography. The chromatographic columns contained an anion exchange medium suitable to separate Hb from non-hemoglobin proteins. The anion exchange media was formed from silica gel. The silica gel was exposed to γ-glycidoxy propylsilane to form active epoxide groups and then exposed to $C_3H_7(CH_3)NCl$ to form a quaternary ammonium anion exchange medium. This method of treating silica gel is described in the *Journal of Chromatography*, 120:321–333 (1976).

Each column was pre-treated by flushing the chromatographic columns with a first buffer which facilitated Hb binding. Then 4.52 liters of the concentrated Hb solution were injected into each chromatographic column. After injecting the concentrated Hb solution, the chromatographic columns were then washed by successively directing three different buffers through the chromatographic columns to produce a Hb eluate, by producing a pH gradient within the columns. The temperature of each buffer during use was about 12.4° C. The buffers were prefiltered through a 10,000 Dalton ultrafiltration membrane before injection onto the chromatographic columns.

The first buffer, 20 mM tris-hydroxymethyl aminomethane (Tris) (pH about 8.4 to about 9.4), transported the concentrated Hb solution into the media in the chromatographic columns to bind the Hb. The second buffer, a mixture of the first buffer and a third buffer, with the second buffer having a pH of about 8.3, then adjusted the pH within chromatographic columns to elute contaminating non-hemoglobin components from the chromatographic columns, while retaining the Hb. Equilibration with the second buffer continued for about 30 minutes at a flow rate of approximately 3.56 lpm per column. The elute from the second buffer was discarded to waste. The third buffer, 50 mM Tris (pH about 6.5 to about 7.5), then eluted the Hb from the chromatographic columns.

The Hb eluate was then directed through a sterile 0.22μ Sartobran Cat # 5232507 G1PH filter to a tank wherein the Hb eluate was collected. The first 3-to-4% of the Hb eluate and the last 3-to-4% of the Hb eluate were directed to waste.

The Hb eluate was further used if the eluate contained less than 0.05 EU/ml of endotoxin and contained less than 3.3 nmoles/ml phospholipids. To sixty liters of ultrapure eluate, which had a concentration of 100 g Hb/l, was added 9 l of 1.0 M NaCl, 20 mM Tris (pH 8.9) buffer, thereby forming a Hb solution with an ionic strength of 160 mM, to reduce the oxygen affinity of the Hb in the Hb solution. The Hb solution was then concentrated at 10° C., by recirculating through the ultrafilter, specifically a 10,000 Dalton Millipore Helicon, Cat # CDUF050 G1 filter, until the Hb concentration was 110 g/l.

The Hb solution was then deoxygenated, until the $pO_2$ of the Hb solution was reduced to the level where $HbO_2$ content was about 10%, by recirculating the Hb solution at 12 lpm, through a 0.05 μm Hoechst-Celanese Corporation Cat # G-240/40) polypropylene microfilter phase transfer membrane, to form a deoxygenated Hb solution (hereinafter "deoxy-Hb"). Concurrently, a 60 lpm flow of nitrogen gas was directed through the counter side of the phase transfer membrane. During deoxygenation, the temperature of the Hb solution was maintained between about 19° C. and about 31° C.

Also during deoxygenation, and subsequently throughout the process, the Hb was maintained in a low oxygen environment to minimize oxygen absorption by the Hb and to maintain an oxygenated Hb (oxyhemoglobin or $HbO_2$) content of less than about 10% in the deoxy-Hb.

The deoxy-Hb, 60 liters) was then diafiltered through an ultrafilter with 180 l of a storage buffer, containing 0.2 wt % N-acetyl cysteine, 33 mM sodium phosphate buffer (pH 7.8) having a $pO_2$ of less than 50 torr, to form a oxidation-stabilized deoxy-Hb. Prior to mixing with the deoxy-Hb, the storage buffer was depyrogenated with a 10,000 Dalton Millipore Helicon, Cat # CDUF050 G1 depyrogenating filter.

The storage buffer was continuously added at a rate approximately equivalent to the fluid loss across the ultrafilter. Diafiltration continued until the volume of fluid lost through diafiltration across the ultrafilter was about three times the initial volume of the deoxy-Hb.

Prior to transferring the oxidation-stabilized deoxy-Hb into a polymerization apparatus, oxygen-depleted WFI was added to the polymerization reactor to purge the polymerization apparatus of oxygen to prevent oxygenation of oxidation-stabilized deoxy-Hb. The amount of WFI added to the polymerization apparatus was that amount which would result in a Hb solution with a concentration of about 40 g Hb/l, when the oxidation-stabilized deoxy-Hb was added to the polymerization reactor. The WFI was then recirculated throughout the polymerization apparatus, to deoxygenate the WFI by flow through a 0.05 μm polypropylene microfilter phase transfer membrane (Hoechst-Celanese Corporation Cat # 5PCM-108, 80 sq. ft.) against a counterflow of pressurized nitrogen. The flow rates of WFI and nitrogen gas, through the phase transfer membrane, were about 18 to 20 lpm and 40 to 60 lpm, respectively.

After the $pO_2$ of the WFI in the polymerization apparatus was reduced to less than about 2 torr $pO_2$, the polymerization reactor was blanketed with nitrogen by a flow of about 20 lpm of nitrogen into the head space of the polymerization reactor. The oxidation-stabilized deoxy-Hb was then transferred into the polymerization reactor.

The polymerization was conducted in a 12 mM phosphate buffer with a pH of 7.8, having a chloride concentration less than or equal to about 35 mmolar.

The oxidation-stabilized deoxy-Hb and N-acetyl cysteine were subsequently slowly mixed with the cross-linking agent glutaraldehyde, specifically 29.4 grams of glutaraldehyde for each kilogram of Hb over a five hour period, while heating at 40° C. and recirculating the Hb solution through a Kenics 1-1/inch static mixer with 6 elements (Chemineer, Inc.), to form a polymerized Hb (poly(Hb)) solution.

Recirculating the oxidation-stabilized deoxy-Hb and the glutaraldehyde through the static mixer caused turbulent flow conditions with generally uniform mixing of the glutaraldehyde with the oxidation-stabilized deoxy-Hb, thereby reducing the potential for forming pockets of deoxy-Hb containing high concentrations of glutaraldehyde. Generally uniform mixing of glutaraldehyde and deoxy-Hb reduced the formation of high molecular weight poly(Hb) (having a molecular weight above 500,000 Daltons) and also permitted faster mixing of glutaraldehyde and deoxy-Hb during polymerization.

In addition, significant Hb intramolecular cross-linking resulted during Hb polymerization as an effect of the presence of N-acetyl cysteine upon the polymerization of Hb.

After polymerization, the temperature of the poly(Hb) solution in the polymerization reactor was reduced to a temperature between about 15° C. to about 25° C.

The poly(Hb) solution was then concentrated by recirculating the poly(Hb) solution through the ultrafilter until the concentration of the poly(Hb) was increased to about 85 g/l. A suitable ultrafilter is a 30,000 Dalton filter (e.g., Millipore Helicon, Cat # CDUF050LT).

Subsequently, the poly(Hb) solution was then mixed with 66.75 g sodium borohydride and again recirculated through the static mixer. Specifically, for every nine liters of poly (Hb) solution, one liter of 0.25 M sodium borohydride solution was added at arate of 0.1 to 0.12 lpm.

Prior to adding the sodium borohydride to the poly(Hb) solution, the pH of the poly(Hb) solution was basified by adjusting pH to a pH of about 10 to preserve the sodium borohydride and to prevent hydrogen gas formation. The pH of the poly(Hb) solution was adjusted by diafiltering the poly(Hb) solution with approximately 215 l of depyrogenated, deoxygenated 12 mM sodium borate buffer, having a pH of about 10.4 to about 10.6. The poly(Hb) solution was diafiltered by recirculating the poly(Hb) solution from the polymerization reactor through the 30 kD ultrafilter. The sodium borate buffer was added to the poly(Hb) solution at a rate approximately equivalent to the rate of fluid loss across the ultrafilter from diafiltration. Diafiltration continued until the volume of fluid lost across the ultrafilter from diafiltration was about three times the initial volume of the poly(Hb) solution in the polymerization reactor.

Following pH adjustment, sodium borohydride solution was added to the polymerization reactor to reduce bonds in the poly(Hb) solution to bonds and to form stable poly(Hb) in solution. During the sodium borohydride addition, the poly(Hb) solution in the polymerization reactor was continuously recirculated through the static mixer and the 0.05 μm polypropylene microfilter phase transfer membrane to remove dissolved oxygen and hydrogen. Flow through a static mixer also provided turbulent sodium borohydride flow conditions that rapidly and effectively mixed sodium borohydride with the poly(Hb) solution. The flow rates of poly(Hb) solution and nitrogen gas through the 0.05 μm phase transfer membrane were between about 2.0 to 4.0 lpm and about 12 to 18 lpm, respectively. After completion of the sodium borohydride addition, reduction continued in the polymerization reactor while an agitator contained therein rotated at approximately 75 rotations per minute.

Approximately one hour after the sodium borohydride addition, the stable poly(Hb) solution was recirculated from the polymerization reactor through the 30,000 Dalton ultrafilter until the stable poly(Hb) solution concentration was 110 g/l. Following concentration, the pH and electrolytes of the stable poly(Hb) solution were restored to physiologic levels to form a stable polymerized Hb blood-substitute, by diafiltering the stable poly(Hb) solution, through the 30,000 Dalton ultrafilter, with a filtered, deoxygenated, low pH buffer containing 27 mM sodium lactate, 12 mM NAC, 115 mM NaCl, 4 mM KCl, and 1.36 mM $CaCl_2$ in WFI, (pH 5.0). Diafiltration continued until the volume of fluid lost through diafiltration across the ultrafilter was about 6 times the pre-diafiltration volume of the concentrated Hb product.

After the pH and electrolytes were restored to physiologic levels, the stable polymerized Hb blood-substitute was then diluted to a concentration of 5.0 g/dl by adding the filtered, deoxygenated low pH buffer to the polymerization reactor. The diluted blood-substitute was then diafiltered by recirculating from the polymerization reactor through the static mixer and a 100,000 Dalton purification filter against a filtered deoxygenated buffer containing 27 mM sodium lactate, 12 mM NAC, 115 mM NaCl, 4 mM KCl, and 1.36 mM $CaCl_2$ in WFI, (pH 7.8). Diafiltration continued until the blood-substitute contained less than or equal to about 10% modified tetrameric and unmodified tetrameric species by GPC when run under dissociating conditions.

The purification filter was run under conditions of low transmembrane pressure with a restricted permeate line. Following removal of substantial amounts of modified tetrameric Hb and unmodified tetrameric Hb, recirculation of the blood-substitute continued through the 30,000 Dalton ultrafilter until the concentration of the blood-substitute was about 130 g/l.

The stable blood-substitute was then stored in a suitable container having a low oxygen environment and a low oxygen in-leakage.

EXAMPLE 2

Hemoglobin Blood-Substitute Storage: Foil Overwrap

The hemoglobin blood-substitute, as prepared in Example 1, packaged in a 600 mL Stericon package, was over-wrapped in a foil laminate package (KAPAK 50303, referred below as "foil"), Cryovac BYV200 or Cryovac P640B package. KAPAK 50303 is foil laminate container wherein the foil layer is aluminum foil. Cryovac BYV200 is a laminate containing a 0.0006 inch two-sided Saran-coated polyvinyl alcohol layer. The oxygen permeability of these two laminates is less than 0.02 cc/100 square inch/24 hrs/atm/72° F./0% humidity. Cryovac P640B is a laminate material comprising a 0.0006 in. Saran-coated, biaxially-oriented Nylon layer, an adhesive and a linear low density polyethylene sealant layer. The oxygen permeability of the material is about 8 to 15 cc/100 sq in/24 hours/atm/72° F./0% humidity. The packaged blood substitutes were maintained at room temperature for about 418 days with periodic sampling of the concentration and/or levels of N-acetyl-L-cysteine (NAC), bis-N-acetyl-L-cysteine ($NAC_2$), total Hb (THb), oxygenated hemoglobin ($HbO_2$) and bin (metHb). The results are set forth in Table II.

TABLE II

Stability Data on Overwraps

| Day | Over-wrap | NAC (%) | $NAC_2$ (%) | THb (g/dl) | $HbO_2$ (%) | metHB (%) |
| --- | --- | --- | --- | --- | --- | --- |
| 0 | Foil | 0.1515 | 0.008 | 10.7 | 4.1 | −0.2 |
| 0 | BYV200 | 0.1586 | 0.0139 | 10.7 | 8.8 | −0.3 |
| 0 | P640B | 0.1274 | 0.0829 | 11.7 | 5.7 | 1.1 |
| 43 | Foil | 0.1688 | 0.0155 | 11.3 | 3.3 | −0.3 |
| 43 | BYV200 | 0.1509 | 0.0365 | 11.1 | 2.7 | 0.3 |
| 43 | P640B | 0.0507 | 0.1927 | 11.2 | 5.6 | 6.2 |
| 117 | Foil | 0.1721 | 0.0136 | 11.7 | 2.6 | 0.0 |
| 117 | BYV200 | 0.1433 | 0.0238 | 11.9 | 3.0 | 0.1 |
| 117 | P640B | 0.0022 | 0.2355 | 12.5 | 12.7 | 30.7 |
| 180 | Foil | 0.1818 | 0.0108 | 12.1 | 2.9 | −0.1 |
| 180 | BYV200 | 0.1674 | 0.0327 | 12.5 | 2.5 | 0.2 |
| 180 | P640B | N.D. | 0.2259 | 12.8 | 18.2 | 49.6 |
| 418 | Foil | 0.15 | 0.05 | 11.6 | 4.5 | 1.2 |
| 418 | BYV200 | 0.17 | 0.04 | 11.8 | 3.7 | 0.5 |
| 418 | P640B | N.D. | 0.19 | 12.0 | −1.3 | 92.3 |

The above experiment was essentially repeated wherein a hemoglobin blood-substitute was overwrapped in a foil laminate package (KAPAK 50303). The packaged blood substitutes were maintained at room temperature for about 24 months with periodic sampling of the concentration and/or levels of N-acetyl-L-cysteine (NAC), bis-N-acetyl-L-cysteine ($NAC_2$), total Hb (THb), oxygenated hemoglobin ($HbO_2$) and lobin (metHb). The results are set forth in Table III.

TABLE III

Stability Data on Foil Overwraps

| Month | NAC (%) | $NAC_2$ (%) | THb (g/dl) | $HbO_2$ (%) | metHB (%) |
| --- | --- | --- | --- | --- | --- |
| 0 | 0.16 | 0.04 | 13.1 | 4 | 3 |
| 3 | 0.13 | 0.04 | 13.4 | 3 | 2 |
| 6 | 0.14 | 0.03 | 13.3 | 3 | 2 |
| 9 | 0.15 | 0.03 | 13.2 | 4 | 2 |
| 12 | 0.13 | 0.06 | 13.3 | 5 | 2 |

TABLE III-continued

Stability Data on Foil Overwraps

| Month | NAC (%) | NAC$_2$ (%) | THb (g/dl) | HbO$_2$ (%) | metHB (%) |
|---|---|---|---|---|---|
| 18 | 0.14 | 0.05 | 13.2 | 3 | 2 |
| 24 | 0.14 | 0.02 | 13.3 | 3 | 2 |

EXAMPLE 3

Hemoglobin Blood-Substitute Storage: Primary Package

The hemoglobin blood-substitute, as prepared in Example 1 was packaged in an oxygen barrier primary package (E-13135 and E13242, American National Can). The construction of the primary package is discussed in detail above. The primary package is a laminate material comprising a medium density polyethylene layer, ethylene vinyl alcohol/nylon layer, and linear low density polyethylene sealant layer.

EXAMPLE 4

Hemoglobin Blood-Substitute Storage: Transparent Overwrap

The hemoglobin blood-substitute, as prepared in Example 1, packaged in a suitable primary package, was overwrapped in a transparent laminate package comprising a polypropylene layer, an ethylene vinyl alcohol layer and a polypropylene layer. An automated packaging machine (Tiromat) was used to generate the overwraps. The oxygen permeability of the material is about 0.00153 cc/100 in$^2$-atm-day (25° C., 100%/50% RH). The packaged blood substitute was maintained at 40° and 100%/60% RH for about 12 months and the concentration and/or levels of N-acetyl-L-cysteine (NAC), bis-N-acetyl-L-cysteine (NAC$_2$), total Hb (THb), oxygenated hemoglobin (HbO$_2$) and methemoglobin (met Hb) were measured. The results are set forth in Table IV. Maintenance of the samples at the elevated temperature of 40° C. for 12 months has the effect of storage for 24 months at 23° C.

TABLE IV

Accelerated Stability Data on Clear (EVOH) Overwrap

| Month | NAC (%) | NAC2 (%) | THb (g/dl) | HbO$_2$ (%) | MetHb (%) |
|---|---|---|---|---|---|
| 0 | 0.15 | 0.02 | 13.4 | 2.4 | 0.8 |
| 3 | 0.12 | 0.06 | 13.3 | 2.5 | 2.0 |
| 6 | 0.06 | 0.13 | 13.5 | 2.3 | 3.9 |
| 9 | 0.06 | 0.19 | 13.7 | 3.0 | 5.6 |
| 12 | 0.02 | 0.20 | 13.9 | 3.7 | 7.9 |

EXAMPLE 5

Polymerized Hemoglobin Analysis

The endotoxin concentration in the hemoglobin product is determined by the method "Kinetic/ Turbidimetric LAL 5000 Methodology" developed by Associates of Cape Cod, Woods Hole, Mass., J. Levin et al., *J. Lab. Clin. Med.*, 75:903–911 (1970). Various methods were used to test for any traces of stroma for example, a precipitation assay, immunoblotting, and enzyme-linked immunosorbent assay (ELISA) for a specific cell membrane protein or glycolipid known by those skilled in the art.

Particulate counting was determined by the method "Particulate Matter in Injections: Large Volume Injections for Single Dose Infusions", *U.S Pharmacopeia*, 22:1596, 1990.

To determine glutaraldehyde concentration, a 400 µl representative sample of the hemoglobin product was derivatized with dinitrophenylhydrazine and then a 100 µl aliquot of the derivative solution was injected onto a YMC AQ-303 ODS column at 27° C., at a rate of 1 ml/min., along with a gradient. The gradient consisted of two mobile phases, 0.1% trifluoroacetic acid (TFA) in water and 0.08% TFA in acetonitrile. The gradient flow consisted of a constant 60% 0.08% TFA in acetonitrile for 6.0 minutes, a linear gradient to 85% 0.08% TFA in acetonitrile over 12 minutes, a linear gradient to 100% 0.08% TFA in acetonitrile over 4 minutes hold at 100% 0.08% TFA in acetonitrile for 2 minutes and re-equilibrate at 45% of 0.1% TFA in water. Ultraviolet detection was measured at 360 nm.

To determine NAC concentration, an aliquot of hemoglobin product was diluted 1:100 with degassed sodium phosphate in water and 50 µl was injected onto a YMC AQ-303 ODS column with a gradient. The gradient buffers consisted of a sodium phosphate in water solution and a mixture of 80% acetonitrile in water with 0.05% TFA. The gradient flow consisted of 100% sodium phosphate in water for 15 minutes, then a linear gradient to 100% mixture of 80% acetonitrile and 0.05% TFA over 5 minutes, with a hold for 5 minutes. The system was then re-equilibrated at 100% sodium phosphate for 20 minutes.

Phospholipid analysis was done by a method based on procedures contained in the following two papers: Kolarovic et al., "A Comparison of Extraction Methods for the Isolation of Phospholipids from Biological Sources", *Anal. Biochem.*, 156:244–250, 1986 and Duck-Chong, C. G., "A Rapid Sensitive Method for Determining Phospholipid Phosphorus Involving Digestion With Magnesium Nitrate", *Lipids*, 14:492–497, 1979.

Osmolarity was determined by analysis on an Advanced Cryomatic Osmometer, Model #3C2, Advanced Instruments, Inc., Needham, Mass.

Total hemoglobin, methemoglobin and oxyhemoglobin concentrations were determined on a Co-Oximeter Model #482, from Instrumentation Laboratory, Lexington, Mass.

Na$^+$, K$^+$, Cl$^-$, Ca$^{++}$, pO$_2$ concentrations were determined by a Novastat Profile 4, Nova Biomedical Corporation, Waltham, Mass.

Oxygen binding constant, P$_{50}$ was determined by a Hemox-Analyzer, TCS Corporation, Southhampton, Pa.

Temperature and pH were determined by standard methods known by those skilled in the art.

Molecular weight (M.W.) was determined by conducting gel permeation chromatography (GPC) on the hemoglobin products under dissociating conditions. A representative sample of the hemoglobin product was analyzed for molecular weight distribution. The hemoglobin product was diluted to 4 mg/ml within a mobile phase of 50 mM Bis-Tris (pH 6.5), 750 mM MgCl$_2$, and 0.1 mM EDTA. This buffer serves to dissociate Hb tetramer into dimers, that have not been cross-linked to other Hb dimers through intramolecular or intermolecular cross-links, from the poly(Hb). The diluted sample was injected onto a TosoHaas G3000SW column. Flow rate was 0.5 ml/min. and ultraviolet detection was recorded at 280 nm.

The results of the above tests on veterinary (OXYGLOBIN™) and human Hb blood-substitutes, formed according to the method of invention, are summarized in Tables V and VI, respectively.

TABLE V

| PARAMETER | RESULTS |
|---|---|
| pH (18–22° C.) | physiologically acceptable pH |
| Endotoxin | <0.5 EU/ml |
| Sterility Test | Meets Test |
| Phospholipids[a] | <3.3 nm/ml |
| Total Hemoglobin | 12.0–14.0 g/dl |
| Methemoglobin | <15% |
| Oxyhemoglobin | <10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Boron | <10 ppm |
| Osmolality | 290–310 mOsm |
| Glutaraldehyde | <3.5 μg/ml |
| N-acetyl-L-cysteine | <0.2% |
| M.W. > 500,000 | <15% |
| Unmodified Tetramer | <5% |
| Particulate Content >10μ | <12/ml |
| Particulate Content >25μ | <2/ml |

[a] measured in Hb before polymerization

TABLE VI

| PARAMETER | RESULTS |
|---|---|
| pH (18–22° C.) | Physiologically acceptable pH |
| Endotoxin | <0.5 EU/ml |
| Sterility Test | Meets Test |
| Phospholipids[a] | <3.3 nm/ml |
| Total Hemoglobin | 12.0–14.0 g/dl |
| Methemoglobin | <15% |
| Oxyhemoglobin | <10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Boron | <10 ppm |
| Osmolality | 290–310 mOsm |
| Glutaraldehyde | <3.5 μg/ml |
| N-acetyl-L-cysteine | $\leq$ 0.2% |
| M.W. >500,000 | $\leq$15 % |
| M.W. $\leq$65,000 | <10% |
| M.W. <32,000 | <5% |
| Particulate Content >10μ | <12/ml |
| Particulate Content >25μ | <2/ml |

[a] measured in Hb before polymerization

EXAMPLE 6

Determination Of In Vivo Oncotic Effects in Canines

The purpose of this study was to determine the in vivo oncotic effects, specifically the volume of water drawn into the intravascular space per gram of hemoglobin administered, of veterinary (OXYGLOBIN™) Hb blood-substitute in splenectomized beagle dogs by measuring the expansion of plasma volume following a toploading dose. In addition, a comparable dose of (RHEOMACRODEX™-Saline), manufactured by Pharmacia, which is 10% Dextran 40 and 0.9% saline, was also determined.

Two dogs were entered into this study after a routine health screening and an acclimatization period of at least four weeks. The dogs were splenectomized at least 3 days before treatment. They were pre-anesthetized, with a combination of atropine and meperidine HCl, and anesthetized via inhalation of isoflurane. Lactated Ringer's solution was infused at 10–20 ml/kg/hr during the surgical procedure.

The dogs received the Hb blood-substitute (40 ml/kg) at 20 ml/kg/hr via a disposable cephalic catheter. Hematocrit was measured pre-do sing and at ¼, ½, 1, 2, 3, 4 hours post-dosing or longer until the nadir of the hematocrit was established.

The dogs were splenectomized to ensure a constant plasma volume and RBC mass to allow accurate measurement of the change in plasma volume following dosing.

Calculation of the change in plasma volume was made using the following equation:

$$\Delta \%PV = \left\{ \frac{Hct_1(1 - Hct_2)}{Hct_2(1 - Hct_1)} - 1 \right\} 100$$

where PV is the plasma volume, $Hct_1$ is the initial hematocrit, and $Hct_2$ is the final hematocrit. This calculation was based on the change in hematocrit, assuming that the number of RBC's within the circulating blood volume and mean corpuscular volume remained constant.

As shown in Table VII, the nadir of the hematocrit occurred two hours post-dosing in both dogs. The mean corpuscular volume (MCV) remained stable throughout the study.

TABLE VII

| | Hematocrit (%) | | MCV (fL) | |
|---|---|---|---|---|
| Time (Hour) | Dog 3503C | Dog 14 Male | Dog 3503C | Dog 14 Male |
| 0 | 46 | 55 | 67.6 | 67.2 |
| ¼ | 41 | 50 | 68.1 | 67.7 |
| ½ | 37 | 48 | 67.5 | 67.2 |
| 1 | 35 | 41 | 68.6 | 67.9 |
| 2 | 31 | 37 | 68.1 | 67.1 |
| 3 | 33 | 39 | 66.8 | 66.1 |
| 4 | 32 | 40 | 66.3 | 65.4 |

The volume of fluid drawn intravascularly post dosing was 6 ml/g hemoglobin and 9 ml/g hemoglobin for dogs 3503C and 14 male, respectively. The dose of synthetic colloid solution (Rheomacrodex®-Saline) was calculated based on a dose that causes a similar oncotic effect. Rheomacrodex draws approximately 22 ml fluid from the interstitium per gram administered intravenously.

The calculated comparable dose of Rheomacrodex was 14 ml/kg and 7 ml/kg for 30 ml/kg and 15 ml/kg Hb blood-substitute, respectively.

The volume of fluid drawn intravascularly by (Oxyglobin™) Hb blood-substitute was 8 ml $H_2O$/gram hemoglobin. Since the volume of the dose was 30 ml/kg, and the concentration of hemoglobin in the dose was 13 g/dl, the total amount of hemoglobin per dose was 3.9 g/kg and the total volume of fluid drawn into the intravascular space/dose by the Hb blood-substitute was 31.2 ml The synthetic colloid solution draws in about 22 ml of water/gram of Dextran. The total amount of Dextran in the colloid solution per comparable dose of Hb blood-substitute is 1.4 g. Thus, the total volume of fluid drawn into intravascular space/comparable dose of colloid solution is 14 ml.

EXAMPLE 7

Canine Dose Response Study

This study was conducted to determine the drug effect and dose response of veterinary (OXYGLOBIN™) Hb bloodsubstitute of this invention, as compared to a synthetic colloid solution, of (RHEOMACRODEX™-Saline, Pharmacia) which is 10% Dextran 40 and 0.9% saline, with respect to arterial oxygen content relative to canine red blood cell hemoglobin and oxygen delivery in splenectomized beagle dogs 60 minutes and 24 hours following acute normovolemic hemodilution.

Acute normovolemic hemodilution is an experimental model that mimics a clinical condition of anemia due to surgical blood loss. Severe anemia (Hct=9%, Hb=3 g/dl) was produced by this method to cause an absolute requirement of oxygen carrying support. Oxygen delivery and oxygen content decreased precipitously with the massive bleeding.

In developing the normovolemic hemodilution model, it was found that treatment to restore oxygen delivery either by volume expansion alone, as was done for the control dogs, or by volume expansion in conjunction with an increase in the arterial oxygen content, as occurred for the dogs treated with hemoglobin solution, had to occur within approximately 10 minutes of reaching a hematocrit of 9% to avoid irreversible decreases in blood pressure and cardiac output which then resulted in death.

Two of 12 control dogs in this study died during or following dosing even though their vascular volume was expanded with Dextran 40 solution within 5 minutes of reaching the targeted hematocrit. The death of these dogs is a reflection of the severity of the experimental model which in turn portrays the clinical condition of severe acute blood loss.

Thirty dogs were entered into this study after a routine health screening and acclimatization period of at least four weeks. Treatment was staggered using three replicates of dogs (A, B and C), each replicate containing one dog/sex/group. Dogs were randomly assigned to the 5 groups (6 dogs/group of 3 males and 3 females) 32 days before the first day of treatment. Dogs were assigned to their respective groups by block randomization based on body weight using a method which ensured equal distribution among groups. Males and females were randomized separately. Any dog with unacceptable pretreatment data, such as abnormal clinical signs or clinical pathology data, was replaced by a spare dog maintained under the same environmental conditions.

The test/control articles were administered by a single intravenous infusion. The rate of infusion was controlled by an infusion pump. The actual volume infused per hour depended upon the most recent body weight of each of the dogs.

The highest dose of hemoglobin solution was based upon the safe upper limit of acute cardiovascular effects due to volume expansion in normovolemic dogs. The midrange dose was chosen to define the shape of the dose response curve. The lowest dose was based on the lower limit of clinically relevant dosing as defined by volume and hemodynamic effects in the dog.

Each dog was splenectomized at least 7 days before treatment to avoid effects on the experimental model of an increased circulatory RBC mass due to splenic contraction. On the day of treatment with hemoglobin solution, each dog was anesthetized by inhalation of isoflurane and mechanically ventilated using room air with a tidal volume of 20–25 ml/Kg. The rate of ventilation was adjusted during the procedure to maintain arterial $pCO_2$ at approximately 40 mmHg. The end-expired concentration of isoflurane was measured and controlled to provide a valid comparison of anesthetic plane from dog to dog. The dogs were instrumented for monitoring of hemodynamic function and oxygen transport parameters. Placement of a flow-directed catheter in the pulmonary artery was confirmed by analysis of pressures and pressure tracings. A dual-lumen catheter, with thermodilution cardiac output capability, was placed in the femoral artery to provide an arterial line for blood pressure monitoring and blood withdrawal. A catheter was placed in the cephalic vein, or other vein if required, for volume replacement and test/control article administration.

Each dog received an intramuscular injection of antibiotics once daily (Procaine penicillin G) prophylactically for one day prior to surgery, on the day of surgery and for 3 days following the splenectomy. V-Sporin, a topical antibiotic (Polymyxin B, Bacitracin, Neomycin) was applied to the surgical site once daily, as needed.

Following instrumentation, hemodynamic stabilization to reach a $pCO_2$ of approximately 40 mm Hg and collection of baseline measurements were performed. A model of acute normovolemic hemodilution was then produced by bleeding the dogs and simultaneously replacing approximately 1.6 to 2.3 times the volumes withdrawn with Lactated Ringer's Solution to maintain isovolemic status. Isovolemic status was achieved by maintaining pulmonary artery wedge pressure at approximately baseline values. The blood withdrawal/volume replacement took approximately 45 to 90 minutes until the hemoglobin concentration was approximately 30 g/l (3.0 g/dl). Lactated Ringer's Solution was infused rapidly using a gravity intravenous set and a pressure cuff around the infusion bag. If the arterial systolic blood pressure was ≦50 mmHg for more than 5 minutes following the induction of acute anemia and prior to the start of dosing, the dog was rejected and replaced by a spare dog maintained under the same environmental conditions.

Doses of colloid control and hemoglobin solution were administered as stated in Table V. Hemodynamic measurements were performed pre-bleed, pre-dose, immediately following dosing, and at 60 minutes and 24 hours following dosing. After the 60 minute measurement, the dog recovered from anesthesia and was instrumented again for hemodynamic measurements, performed at 24 hours following dosing.

TABLE VIII

| Group | Test Article | Dose Volume ml/Kg | Dose Rate ml/Kg/h | Animals/Group Males Females |
|---|---|---|---|---|
| 1 | Colloid control (mid dose) | 14 | 20 | 3 3 |
| 2 | Colloid control (low dose) | 7 | 20 | 3 3 |
| 3 | Hb blood-substitute (low dose) | 15 | 20 | 3 3 |
| 4 | Hb blood-substitute (mid dose) | 30 | 20 | 3 3 |
| 5 | Hb blood-substitute (high dose) | 45 | 20 | 3 3 |

All hemodynamic parameters were statistically analyzed by either analysis of variance (ANOVA) or analysis of covariance (ANCOVA) with either the pre-bleeding or pre-dosing value as the covariate. Specific linear contrasts were constructed to test for the effects of volume of the solution administered, the effect of Hb blood-substitute (drug effect), and the dose response of the Hb blood-substitute (dose effect). These tests were performed only for parameters for which the difference among experimental groups was statistically significant at the 0.05 level. Comparisons of specified variables at selected time points were performed by paired t-tests in each group.

Arterial oxygen content was one criterion of efficacy in this study. Arterial oxygen content is a measure of the oxygen carrying capacity of cellular and plasma hemoglobin and dissolved oxygen in the plasma. In the absence of plasma hemoglobin, arterial oxygen content is calculated from the amount of oxygen carried by saturated cellular hemoglobin and the partial pressure of inspired oxygen. Because plasma hemoglobin was expected to contribute significantly to oxygen content in this study, oxygen content was measured directly using a LexO2Con-K instrument (Chestnut Hill, Mass.). Oxygen enriched air was not administered during the experiment because it was unnecessary and to avoid the confounding effects of an increased inspired oxygen concentration on the measurement of arterial oxygen content.

Mean arterial and venous oxygen contents decreased approximately four and eight times, respectively in all groups following induction of anemia. Arterial oxygen content increased significantly 60 minutes following dosing compared to pre-dosing values in all Hb blood-substitute treated groups and remained significantly increased at 24 hours following dosing in the mid and high dose groups. Arterial or venous oxygen content did not change following dosing in either control group.

Arterial oxygen content was significantly increased in Hb blood-substitute treated groups compared to control groups at 60 minutes and 24 hours following dosing. A linear dose response was seen at 60 minutes and 24 hours following dosing. A significant volume effect was detected for arterial oxygen content 60 minutes following dosing.

Venous oxygen content also significantly increased in Hb blood-substitute treated groups compared to controls at 60 minutes and 24 hours following dosing. The increase showed a linear dose response at 60 minutes following dosing but not at 24 hours.

The dose effect observed for Hb blood-substitute treated groups in arterial-venous (A-V) oxygen content difference at 60 minutes following dosing was attributed to significant volume effects based on the absence of a drug effect and similar observations of volume effects in control groups at 60 minutes following dosing. Hb blood-substitute treated groups showed a significant increase in A-V oxygen difference at 24 hours compared to colloid controls, with a significant linear dose response. The A-V difference must be interpreted in view of the cardiac output. At 24 hours following dosing, the A-V difference in the control groups was significantly lower than that of the Hb blood-substitute treated groups. One possible explanation for this difference is that the control group dogs had to rely on a higher cardiac output to meet the oxygen consumption needs of peripheral tissues. The Hb blood-substitute treated groups maintained a large enough A-V difference at 24 hours following dosing to meet peripheral tissue needs without cause for an increased cardiac output.

In addition to arterial oxygen content, total arterial oxygen content normalized relative to the contribution of canine RBC hemoglobin ($CaO_2$/g RBC Hb) was examined in this study. This comparison was made to demonstrate differences in arterial oxygen content among dosing groups since the RBC hemoglobin was constant in all groups. The potential correlation of plasma or total hemoglobin concentration and arterial oxygen content would provide a useful clinical measure of efficacy. At 60 minutes and 24 hours following dosing, all Hb blood-substitute treated groups (except the low dose group at 24 hours) showed a significant increase in $CaO_2$/g RBC hemoglobin to pre-dosing values. Arterial oxygen content relative to that contributed by RBC hemoglobin did not differ significantly in the colloid controls between pre-dose and 60 minutes or 24 hours following dosing.

Total arterial oxygen content relative to that contributed by red blood cell hemoglobin significantly increased in Hb blood-substitute treated groups compared to colloid controls at 60 minutes following dosing with a significant linear dose response. A significant dose effect also occurred at 24 hours following dosing with a significant linear dose response, but the drug effect was not quite significant ($P<0.06$).

Oxygen delivery was another criterion of efficacy. Oxygen delivery is calculated based on arterial oxygen content and cardiac output. Therefore, oxygen delivery is affected by all the physiologic factors which influence cardiac output. The control chosen for this study was the synthetic colloid (RHEOMACRODEX™-Saline, Pharmacia) which is 10% Dextran 40 and 0.9% saline, as it expands intravascular volume and is not known to carry oxygen. The control provided a comparison of equivalent volume expansion to the colloidal properties of the hemoglobin in Hb blood-substitute.

Because each dose of Hb blood-substitute was expected to demonstrate a distinct volume effect, two doses of dextran solution were used as controls for the volume effect so the data would reflect only the drug effect of different doses. This comparison was made for the low and mid doses. The doses of colloid controls were selected based on those doses of Dextran 40 which provided an equivalent comparison of the in vivo oncotic effects of the low and mid-dose test articles, as determined from the results of Example 2.

The volume effect was defined statistically using the difference in means between the colloid mid dose (14 ml/kg) and the colloid low dose (7 ml/kg). The drug effect was determined by comparing each Hb blood-substitute treated group to its corresponding colloid control. A linear dose response was established when a statistically significant difference was seen between the low and high dose Hb blood-substitute treated groups.

Oxygen delivery was calculated according to the equation: $DO_2 = CO \times CaO_2 \times 10$/kg where CO is the cardiac output and $CaO_2$ is the arterial oxygen content. As expected, following induction of anemia in all treatment groups, a two to three fold mean decrease in $DO_2$ occurred in all groups. The oxygen content decreased sufficiently that the maintenance of baseline oxygen consumption had to result from an increase in cardiac output and increased extraction of oxygen, resulting in a lower venous oxygen content. Oxygen delivery increased approximately 30% in the low dose Hb blood-substitute treated group and greater than 100% in the mid and high Hb blood-substitute treated groups at 60 minutes following dosing compared to pre-dosing values. The difference was significant for all three dosing groups ($p<0.05$). The control groups showed no significant differences over this time. At 60 minutes following dosing, $DO_2$ differed significantly among all groups with significant drug and dose effects with a linear dose response. At 24 hours, no difference in oxygen delivery was noted among groups. The improvement in oxygen delivery at 60 minutes following dosing for all Hb blood-substitute treated groups, as compared to their corresponding colloid controls, was due primarily to a dose related increase in arterial oxygen content in addition to a modest increase in cardiac output.

Oxygen consumption was calculated according to the equation: $VO_2 = CO \times CaO_2 33$ 10 kg. A two to three fold mean decrease in $DO_2$ occurred in all groups following the induction of anemia. No statistically significant differences were noted among Hb blood-substitute treated or control groups or within a group when comparing pre-dosing to post-dosing values.

The Oxygen Extraction Ratio ($VO_2/DO_2$) for all groups showed an approximately three fold increase following induction of anemia. Oxygen extraction ratios were significantly decreased in a dose dependent manner in all Hb blood-substitute treated groups at 60 minutes following dosing compared to control groups. No significant differences were noted between Hb blood-substitute treated and control groups at 24 hours following dosing.

Mean cardiac output increased between 10% and 39% in all groups following induction of anemia. Cardiac output was significantly increased at 24 hours following dosing compared to pre bleeding values in the colloid control groups but not in the Hb blood-substitute treated groups. A significant volume effect which contributed to significant differences in cardiac output between colloid low and mid dose groups was evident at 60 minutes post-dosing. The increase in cardiac output was likely related to an increased stroke volume due to expansion of the intravascular volume following dosing or increased sympathetic tone due to the stress of severe anemia. A significant dose response between Hb blood-substitute low and high dose groups was apparent at 60 minutes, but not at 24 hours following dosing. No difference in cardiac output between Hb blood-substitute treated and colloid control groups was seen at 60 minutes or 24 hours following dosing.

Pulmonary artery wedge pressure (PAWP) did not change significantly during the induction of anemia. PAWP decreased significantly in the low dose colloid group and remained unchanged in the mid dose colloid group 60 minutes following dosing compared to pre dosing values. The PAWP in the mid and high dose Hb blood-substitute treated groups increased significantly in a linear dose response compared to pre-dosing values at 60 minutes following dosing. The increased PAWP reflected a dose dependent increase in intravascular volume at 60 minutes following dosing. No significant drug effect was detected between Hb blood-substitute treated and control groups at 60 minutes or 24 hours following dosing. A significant volume effect was detected in the colloid control groups at 60 minutes following dosing.

Systolic, diastolic and mean arterial blood pressure decreased significantly in all groups following induction of anemia, then increased significantly immediately following dosing. The decrease in systolic arterial blood pressure after the induction of anemia was likely related to a decrease in peripheral vascular resistance due to decreased blood viscosity, a consequence of anemia. At 60 minutes following dosing, the systolic, diastolic, and mean arterial blood pressures of both colloid control groups did not differ significantly from pre-dosing values. The systolic, diastolic, and mean pressures of the low dose colloid control increased significantly compared to pre-dosing values at 24 hours following dosing. In contrast, the increase in systolic, diastolic, and mean pressures was statistically significant in all Hb blood-substitute treated groups at 60 minutes and 24 hours following dosing compared to pre-dosing values. The systolic, diastolic and mean blood pressures of Hb blood-substitute treated groups were significantly higher than corresponding colloid control groups at 60 minutes following dosing, but not at 24 hours.

Significant increases in systolic, diastolic and mean pulmonary arterial pressures were observed in the mid and high dose Hb blood-substitute treated groups 60 minutes post dosing compared to pre dosing values. The increases persisted at 24 hours post-dosing in the mid Hb blood-substitute treated group for pulmonary diastolic arterial pressure. Additionally the low-dose colloid group showed a statistically significant increase at 24 hours post-dosing compared to pre-dosing values for mean pulmonary artery pressure. This increase was considered clinically significant. The increases in systemic arterial systolic and diastolic blood pressure 60 minutes following dosing of Hb blood-substitute, compared to pre-dosing values, were a direct drug effect of the Hb blood-substitute. The diastolic pressure remained unchanged in the colloid control groups which was probably a result of a decreased peripheral vascular resistance.

No significant differences were found between Hb blood-substitute treated and control groups for pulmonary systolic arterial pressure at either 60 minutes or 24 hours post-dose. In contrast, pulmonary diastolic and mean arterial pressures were significantly different with regard to volume, drug, and dose effects at 60 minutes post dosing, but not at 24 hours.

Total hemoglobin decreased approximately four times or greater with bleeding. Hb blood-substitute treated groups showed a dose dependent increase in total hemoglobin compared to corresponding colloid control groups at 60 minutes and 24 hours following dosing.

Plasma hemoglobin concentrations significantly increased in a dose dependent manner in Hb blood-substitute treated groups compared to corresponding colloid control groups at 60 minutes and 24 hours following dosing. The increases in plasma and total hemoglobin concentrations following dosing in all Hb blood-substitute treated groups, as compared to their corresponding colloid controls, were attributable to the hemoglobin content of Hb blood-substitute. The dose dependent significant increase persisted for 24 hours, correlating with the persistent increase in arterial oxygen content.

In summary, the response to treatment with the Hb blood-substitute was linear, i.e., at 60 minutes following dosing, the higher the dose of Hb blood-substitute the greater the improvement in oxygen delivery and hemodynamics compared to corresponding colloid controls. Sustained arterial oxygen content and normal clinical signs, while breathing room air, support a beneficial biological effect of Hb blood-substitute lasting 24 hours in the 30 ml/kg and 45 ml/kg dose Hb blood-substitute treated groups. The clearance of Hb blood-substitute likely accounts for the changes seen in oxygen delivery and hemodynamic effects at 24 hours following dosing. In conclusion, results from this study support selection of a dose ranging from 30 to 45 ml/kg. Both of these dosing groups showed statistically significant differences from corresponding colloid control groups in the parameters of efficacy and the dose response was linear.

The clinical rationale of this dosing range is based on the fact that a severely anemic dog (e.g., hematocrit <15% with marked clinical signs) would benefit from a higher dose as demonstrated by the linear dose response of improved arterial oxygen content and oxygen delivery. However, a more conservative dose would be indicated for a dog which may be predisposed to intravascular volume overload. The dose dependent transient increase in pulmonary artery wedge pressure and pulmonary arterial pressures seen 60 minutes following dosing in Hb blood-substitute treated groups would limit the use of a higher dose in this population of dogs. Therefore a dosing range of 30–45 ml/kg would be effective in a broad population of dogs in which the degree of anemia and intravascular volume status are defined.

EXAMPLE 8

Human Dose Response Study

This study was conducted to evaluate the safety and tolerance of increasing rates of intravenous administration of Hb blood-substitute (hereinafter HBOC) upon hemodynamic, neuroendocrine and hematologic parameters in humans. The test subjects were normal healthy adult males (70–90 kg) between the ages of 18–45 years. During the study, the test subjects were on controlled isocaloric diets of 55% carbohydrates, 30% fat (polyunsaturated to saturated fat ratio of 2:1), 15% protein and 150 mEq of sodium per day. Fluid intake was at least 3000 mls/day with caffeine containing beverages avoided. Also concomitant use of medication was avoided. Further no alcohol or tobacco were used by the test subjects during the study.

The 12 subjects studied, were divided into three test groups. In each test group, three subjects received HBOC and one served as a control, receiving Ringer's lactate. Each test group had different rates of HBOC infusion. The study was conducted as a single-blind, rate escalation study over a thirty day interval.

On Day 1 of the study, during the inpatient phase, each subject had a small gauge arterial catheter inserted in the radial artery of the non-dominant hand. The insertion location was cleansed with an antiseptic solution (alcohol and/or iodine) and then a small amount of 1%–2% Lidocaine anesthetic solution was subcutaneously injected over the site of the radial artery. The arterial catheter was inserted to monitor blood pressure and to facilitate blood gases evaluations. One to two hours later, all subjects had one large-bore intravenous catheter (16-gauge needle in antecubital fossa) placed in a vein in one arm. Each subject then had a phlebotomy of 750 ml (1.5 units) of whole blood drawn in less than 15 minutes, which was then followed with isovolemic hemodilution by the infusion of 2250 ml of Ringer's lactate over a 2 hour period.

Forty-five grams (346 ml) of HBOC were then intravenously infused using sterile technique, in series through a standard 80 micrometer blood filter, a 5 micrometer filter, and the large-bore intravenous catheter in the arm vein, into each subject in the test groups 1, 2 and 3 at the rates of 0.5 gm/minute, 0.75 gm/minute and 1.0 gm/minute, respectively.

Simultaneously, each subject had invasive monitoring by radial artery catheter, serial pulmonary function tests, cardiac function evaluation and multiple hematology, chemistry and urinalysis laboratory tests which were routinely and frequently performed over the first 28 hours after commencing HBOC infusion.

Subsequently, in the outpatient phase (Days 2–29), laboratory studies, vital signs, ECGs and medical events were taken daily for the first four days post-discharge and then on a weekly basis for a month.

Hemodynamics were remarkable for generally higher values for systolic, diastolic and mean arterial pressure in the HBOC-treated groups (after infusion) than controls during Day 1. Although there was marked variability in the blood pressure data commensurate with patient activity (e.g., during meals or when using the bathroom) and diurnal rhythm, HBOC-treated subjects generally had values for the systolic blood pressure (about 5–15 mm Hg), diastolic blood pressure (about 5–10 mm Hg) and mean arterial pressure (about 10 mm Hg) greater than controls only during the course of Day 1. Values tended to reach peak effects between Hours 8–12 with return to baseline during sleep and upon removal of the arterial catheter. Pulse was generally about 10 beats lower in all HBOC-treated groups compared to controls during Day 1. The nadir of pulse decline was seen within the first 15 minutes of the infusion. Values were similar in all test groups after hour 24.

Cardiac index declined about 1–2 l/min/m$^2$ during the first hour of infusion remained up to 1 l/min/m$^2$ lower than controls through hour 4, and then it returned to baseline by hour 4. Cardiac index also increased during times of patient activity (as above).

Total peripheral resistance paralleled blood pressure changes, however, values returned to baseline within two hours. The transient increase in systemic blood pressure with an increase in total peripheral resistance and decrease in cardiac index is not unexpected. It is important to note that there was no difference in the rate of administration and the magnitude of these hemodynamic responses and that no intervention was indicated.

The pulmonary function tests (including multiple determinations of spirometry and lung volumes) and arterial blood gas measurements were unremarkable. What was noteworthy was the enhanced diffusion capacity that was seen in the HBOC-treated groups. The 10–15% increase in diffusion capacity was statistically significant compared to a 10% decrease in the controls for up to 24 hours. These findings are particularly important because of the magnitude of phlebotomy and hemodilution that all of the groups underwent.

In hematological studies, other than the expected, transient decline in hemoglobin, hematocrit, red cell count and serum proteins with the phlebotomy and hemodilution procedures, the hematology and serum chemistry laboratory tests were unremarkable. Exceptions were serum iron and ferritin which showed peak values by Hours 6 and 48, respectively, after HBOC was given.

The serum chemistry measurements were unremarkable, with the exception of one subject (#10) who had transient increases in serum transaminases and lipase. It is important to note that this subject did not have any clinically significant concomitant medical events (e.g., dysphagia or abdominal pain) commensurate with the time of the elevation of these enzymes. The exact etiology of these laboratory abnormalities is unclear, but previous studies suggest that transient subclinical spasm of the sphincter of Oddi or other portions of the hepatobiliary and pancreatic ductal systems may be involved. It is important to note that these changes were transient (and unaccompanied by abdominal discomfort) and without apparent sequelae. No significant change was noted in Subject #10's post-dose ultrasound of the gall bladder.

Urinalysis was unremarkable throughout the study. There was no detectable urinary hemoglobin in the subjects during the study. In addition, creatinine clearance was slightly higher, as expected, during the hemodilution period), urinary adenosine deaminase binding protein, electrolytes (sodium, potassium, chloride), iron, microalbumin, NAG (N-acetyl-beta-glucosaminidase) and urinary urea nitrogen were unremarkable.

No apparent changes in the majority of the pharmacokinetic parameters were observed as a function of administration rate. Sequential blood specimens and cumulative urine specimens were collected prior to and following initiation of infusion of HBOC for size exclusion (gel filtration) chromatographic (SEC) analysis of total hemoglobin and apparent molecular weight fractions of hemoglobin. Only sporadic plasma dimmer fraction concentrations were observed precluding any pharmacokinetic analysis. The only statistically significant differences ($p<0.05$) were observed in the tetramer volume of distribution (decreases with increases in rate), tetramer maximum concentration achieved (increases with increases in rate) and the time of the tetramer maximum concentration occurrence (decreases with increases in rate).

The observed medical events were consistent with expected findings related to phlebotomy (e.g., vasovagal episode), multiple pulmonary function tests (aerophagia, eructation or abdominal "gas"), arterial line insertion (e.g., pain or tingling over the site), or abdominal discomfort (e.g., associated with the ingestion of the iron supplement). Although there seemed to be a background of nonspecific, transient abdominal "gas." there were no cases of overt abdominal pain or dysphagia. In addition there was no correlation of these symptoms with any alterations in serum transaminases or lipase.

In summary, HBOC was well tolerated. Although there were small transient increases in blood pressure and total peripheral resistance with commensurate decline in cardiac index during the first two hours of the infusion, the hemodynamics were unremarkable. The increase in diffusion capacity was significantly higher in the HBOC-treated groups than controls during the first 24 hours.

EXAMPLE 9

Effects of HBOC on Humans in Graded Bicycle Exercise Testing

This study was conducted to evaluate the exercise capacity of subjects given autologous transfusion of HBOC. Specific endpoints included pulmonary function (e.g., diffusion capacity and lactic acid levels and $pO_2$), hemodynamics (e.g, heart rate, cardiac index and blood pressure) and exercise tolerance (e.g., duration, workload and anaerobic threshold). The subjects were six normal healthy male humans, ages 18–45 years. One subject was replaced in the study due to failure to obtain the volume of phlebotomy in less than 15 minutes. The study was conducted as a randomized, single-blind, two-way crossover study.

All subjects had phlebotomy of 750 ml followed by Ringer's Lactate [3:1] and either an autologous trans-fusion (ATX) or 45 gms of HBOC. The ATX or HBOC was given at 0.5 gm/min for 90 minutes. Bicycle exercise stress tests were done on the day prior to phlebotomy and approximately 45 minutes after the infusion of ATX or HBOC. The same procedures were repeated one week later and subjects were crossed over to the opposite treatment.

On the day of dosing (Days 1 and 8), all subjects had insertion of an arterial line in one radial artery, attachment to cardia telemetry and impedance cardiography and then phlebotomy (PBX) of 750 ml of whole blood (<15 minutes). This was followed by an infusion of 2250 ml of Ringer's lactate (RL) over two hours (the isovolemic hemodilution phase). Subjects then received either HBOC (45 gms [about 346–360 ml] at a rate of 0.5 gm/min over 90 minutes) or an ATX (110–120 gms of hemoglobin [about 750 ml] at the same rate and duration a the HBOC). The BEST was done about 45 minutes after the end of either infusion. Serial measurements of arterial blood gases, hematology, chemistry and urine tests were made intensively during the 24 hour period on Days 1 and 8. Serial follow-up was done on an outpatient basis between the dosing and for one month after all dosing was complete.

Subjects were able to exercise to similar levels during HBOC and ATX periods. The oxygen uptake ($VO_2$) and carbon dioxide production ($VCO_2$) at anaerobic threshold were nearly identical. The actual workload in METS, watts, pulse (as a % of maximum pulse), time to anaerobic threshold, tidal volume (VT) and minute ventilation (VE) were also similar. Arterial blood gas values were similar during the HBOC and ATX periods. The small reductions in pH and bicarbonate with increase in lactic acid is consistent with expected findings at anaerobic threshold. The results of these bicycle tests showed that exercise capacity (defined as time and workload to reach anaerobic threshold) was similar at baseline and after infusions of either autologous transfusion or HBOC. Specifically, hemodynamics were remarkable for slightly higher values (~5 mmHg) during the HBOC period for systolic, diastolic and mean arterial pressure. Commensurate with the increase in blood pressure was an increase in total peripheral resistance, generally within the first 4 hours. Cardiac index declined during the HBOC period (~0.5 l/min/$M^2$). Pulse was about 5–10 beats lower during the HBOC than the ATX period. These findings have been observed in the HBOC studies and have been of little clinical concern.

Pulmonary function tests were unremarkable except for a 14% increase above baseline in diffusion capacity after the ATX and HBOC infusions. Subjects were able to achieve similar exercise capacity during HBOC and ATX periods. Arterial blood gas measurements during peak exercise (anaerobic threshold) were similar in both periods, but arterial $pO_2$ tended to be higher during the HBOC period. Plasma lactic acid levels were lower during the HBOC than ATX period. Resting metabolic art measurements indicated that oxygen consumption, carbon dioxide production and metabolic energy expenditure were greater during the HBOC than ATX period. The comparison as mentioned above is roughly one gram of HBOC to 3 grams of ATX. The diffusion capacity coupled with the observations about $VO_2$ and $VCO_2$ indicate that more oxygen is being delivered to the tissue level per gram of HBOC than ATX. It is commonly held that the diffusion capacity varies directly with the hemoglobin level, however, there is a suggestion that 1 gram of plasma hemoglobin may increase diffusion capacity as much as 3 gms of RBC hemoglobin.

Laboratory studies were notable for small, but transient increases in ALT, AST, 5'-nucleotidase, lipase and creatine kinase during the HBOC period. There were no abnormal urinary finding.

Hematological studies were consistent with those in Example 7.

The observed medical events were consistent with expected findings related to the phlebotomy (e.g., vasovagal episode), multiple pulmonary function tests (eructation or abdominal "gas"), arterial line insertion (e.g., pain or tingling over the insertion site) or numerous everyday complaints that one might observe in normal subjects over the course of a month (e.g., headache, upper respiratory tract infection or cold). The one subject (Subject #105) that had abdominal "gas" and pressure in the mid-epigastrium, but without dysphagia is suggestive of other gastrointestinal complaints that have been observed in previous HBOC studies. L-arginine was used as a therapeutic measure based on the concept that hemoglobin can interfere with endogenous nitric oxide function (nitric oxide is integral in the relaxation of gastrointestinal smooth muscle, especially in the esophagus and intestines). L-arginine is the substrate upon which nitric oxide synthase produces nitric oxide. Theoretically, if one has a reduction in nitric oxide from the hemoglobin (perhaps binding of heme to nitric oxide), then administration of L-arginine might be of benefit. Apparently the subject did get marked by transient relief from his symptoms with the L-arginine for about two hours. This is not an unexpected finding because the plasma half-life of L-arginine is about an hour. Unfortunately, some of the side effects (nausea and vomiting) occurred and the infusion was stopped. We elected to give him a two doses of an anticholinergic, antispasmodic drug, hyoscyamine. This apparently continued to reduce the symptoms of abdominal "gas" and pressure. The subject had no further complaints or sequelae.

In summary, HBOC was associated with improved oxygen delivery and utilization during exercise and at rest. HBOC produced a similar spectrum of hemodynamic, safety laboratory results, pharmacokinetics and medical events to what has previously been observed. Intervention with L-arginine may produce a reversal of gastrointestinal symptoms, but its use was limited by nausea and vomiting. However, the use of anticholinergic therapy might be of value in the treatment for the gastrointestinal symptoms that are encountered.

Those skilled in the art will recognize, or be able to ascertain using no more than routine experimentation, many equivalents to the specific embodiments of the invention described herein. These and all other such equivalents are intended to be encompassed by the following claims.

What is claimed is:

1. A method for preserving a deoxygenated hemoglobin blood substitute comprising maintaining the deoxygenated hemoglobin blood substitute in an oxygen barrier film overwrap including a transparent laminate material having a thickness of between about 0.001 and about 0.01 inches, said laminate material including an ethylene vinyl alcohol layer and having an oxygen permeability of less than about 0.01 cubic centimeters per 100 square inches over 24 hours at one atmosphere and at room temperature.

2. The method of claim 1 wherein the laminate material further includes a polyolefin layer.

3. The method of claim 1, wherein the polyolefin layer and the ethylene vinyl alcohol layer are co-extruded.

4. The method of claim 1, wherein the laminate further includes a linear low density polymer layer.

5. The method of claim 1 wherein the hemoglobin blood substitute is maintained under a nitrogen, argon or helium atmosphere.

6. A preserved deoxygenated hemoglobin blood substitute, comprising:

a) a deoxygenated hemoglobin blood substitute contained within a primary package; and b) a transparent oxygen barrier film overwrap package that includes a first polymer layer, an oxygen barrier film and a second polymer layer, said oxygen barrier film including ethylene vinyl alcohol and having an oxygen permeability of less than about 0.01 cubic centimeters per 100 square inches over 24 hours at one atmosphere and at room temperature, within which the deoxygenated hemoglobin blood substitute and the primary package are sealed, thereby preserving the deoxygenated hemoglobin blood substitute in an environment that is substantially free of oxygen.

7. The preserved deoxygenated blood substitute of claim 6 wherein the first polymer layer includes a polyolefin.

8. The method of claim 6, wherein the first polymer layer and the oxygen barrier layer are co-extruded.

9. The method of claim 6, wherein the second polymer layer includes a polyolefin.

* * * * *

UNITED STATES PATENT AND TRADEMARK OFFICE
CERTIFICATE OF CORRECTION

PATENT NO. : 6,288,027 B1 Page 1 of 1
DATED : September 11, 2001
INVENTOR(S) : Maria S. Gawryl, Robert A. Houtchens and William R. Light It is certified that error appears in the above-identified patent and that said Letters Patent is hereby corrected as shown below:

Column 36,
Line 32, delete "method" and insert therefor -- preserved deoxygenated hemoglobin blood substitute --.
Line 34, delete "method" and insert therefor -- preserved deoxygenated hemoglobin substitute --.

Signed and Sealed this

Twelfth Day of August, 2003

JAMES E. ROGAN
*Director of the United States Patent and Trademark Office*